(12) United States Patent
Li et al.

(10) Patent No.: US 10,392,592 B2
(45) Date of Patent: Aug. 27, 2019

(54) MICROFLUIDIC SCREENING SYSTEM

(71) Applicant: University of Macau, Macau (MO)

(72) Inventors: Cheuk-Wing Li, Macau (MO); Ming Yuen Lee, Macau (MO); Guodong Yu, Macau (MO)

(73) Assignee: University of Macau, Macau (MO)

(*) Notice: Subject to any disclaimer, the term of this patent is extended or adjusted under 35 U.S.C. 154(b) by 174 days.

(21) Appl. No.: 15/806,381

(22) Filed: Nov. 8, 2017

(65) Prior Publication Data

US 2018/0127699 A1    May 10, 2018

Related U.S. Application Data

(60) Provisional application No. 62/419,489, filed on Nov. 9, 2016.

(51) Int. Cl.
*A01K 61/00*    (2017.01)
*C12M 3/06*    (2006.01)
(Continued)

(52) U.S. Cl.
CPC ............ *C12M 23/16* (2013.01); *A01K 1/031* (2013.01); *A01K 61/17* (2017.01); *A01K 63/003* (2013.01);
(Continued)

(58) Field of Classification Search
CPC ...... A01K 63/003; A01K 61/59; A01K 61/10; A01K 63/00; A01K 61/17; A01K 63/006; A01K 63/04; C12M 23/16
(Continued)

(56) References Cited

U.S. PATENT DOCUMENTS

| 3,122,126 A | * | 2/1964 | Yamada | ............... B01F 3/0473 |
| | | | | 119/225 |
| 3,658,034 A | * | 4/1972 | Day | ...................... A01K 61/59 |
| | | | | 119/209 |

(Continued)

FOREIGN PATENT DOCUMENTS

| WO | 2006/097749 A1 | 9/2006 |
| WO | 2010/008977 A2 | 1/2010 |

OTHER PUBLICATIONS

Wang et al.; A Novel Danshensu Derivative Prevents Cardiac Dysfunction and Improves the Chemotherapeutic Efficacy of Doxorubicin in Breast Cancer Cells; Journal of Cellular Biochemistry; 2016; vol. 117, Issue 1; pp. 94-105.

(Continued)

*Primary Examiner* — Yvonne R Abbott-Lewis
*Assistant Examiner* — Yvonne Abbott
(74) *Attorney, Agent, or Firm* — Spruson & Ferguson (Hong Kong) Limited

(57) ABSTRACT

Provided is a microfluidic device comprising an incubation layer, the incubation layer including at least one dock, each of the at least one dock defines a stepped tank comprising an upper tank and a lower tank, an inflow channel in fluid communication with the stepped tank for supplying a fluid to the stepped tank, and an outflow channel in fluid communication with the stepped tank for draining the fluid from the stepped tank, wherein the geometry of the upper tank is configured to allow culturing of a fish larva therein, and wherein the geometry of the lower tank is configured to reversibly receive the fish larva from the upper tank and to dock the fish larva at a controlled orientation for imaging or observation.

20 Claims, 20 Drawing Sheets

(51) Int. Cl.
| | |
|---|---|
| A01K 61/17 | (2017.01) |
| A01K 1/03 | (2006.01) |
| A01K 63/00 | (2017.01) |
| A61K 49/00 | (2006.01) |
| B01L 3/00 | (2006.01) |
| C12M 1/00 | (2006.01) |
| C12M 1/26 | (2006.01) |
| G01N 33/50 | (2006.01) |

(52) U.S. Cl.
CPC ........ *A61K 49/0008* (2013.01); *B01L 3/5025* (2013.01); *B01L 3/5027* (2013.01); *B01L 3/50273* (2013.01); *B01L 3/502715* (2013.01); *B01L 3/502761* (2013.01); *C12M 23/40* (2013.01); *C12M 33/22* (2013.01); *C12M 47/04* (2013.01); *G01N 33/5088* (2013.01); *B01L 2200/0663* (2013.01); *B01L 2200/0694* (2013.01); *B01L 2300/087* (2013.01); *B01L 2300/0858* (2013.01); *B01L 2300/0861* (2013.01); *B01L 2300/0864* (2013.01); *B01L 2300/0874* (2013.01); *B01L 2400/0622* (2013.01); *G01N 2333/4603* (2013.01)

(58) Field of Classification Search
USPC ....... 119/225, 209, 216, 217, 218, 224, 226, 119/232, 245, 248, 253
See application file for complete search history.

(56) References Cited

U.S. PATENT DOCUMENTS

| | | | | |
|---|---|---|---|---|
| 3,797,458 | A * | 3/1974 | Day ........................ | A01K 61/59 119/209 |
| 3,848,567 | A * | 11/1974 | Garber, Jr. ........... | A01K 63/003 119/260 |
| 4,038,945 | A * | 8/1977 | Taborsky ............... | A01K 61/10 119/224 |
| 5,083,528 | A * | 1/1992 | Strong .................. | A01K 63/003 119/225 |
| 5,189,981 | A * | 3/1993 | Ewald, Jr. ............ | A01K 63/003 119/225 |
| 5,197,409 | A * | 3/1993 | Hammond ........... | A01K 63/003 119/245 |
| 5,469,810 | A * | 11/1995 | Chiang ................. | A01K 63/003 119/225 |
| 5,894,936 | A * | 4/1999 | Sanders ..................... | B07B 1/24 209/270 |
| 2006/0102086 | A1* | 5/2006 | Abraham ............. | A01K 63/003 119/217 |
| 2007/0264705 | A1 | 11/2007 | Dodgson | |
| 2009/0098541 | A1 | 4/2009 | Southern | |
| 2011/0269226 | A1 | 11/2011 | Van Noort | |
| 2012/0164679 | A1 | 6/2012 | Vrouwe | |

OTHER PUBLICATIONS

Extended European Search Report of EP application No. 17200530.8 issued from the European Patent Office on Feb. 16, 2018.
Zhu et al.; Fishing on Chips: Up-and-Coming Technological Advances in Analysis of Zebrafish and Xenopus Embryos; Cytometry Part A; 2014; vol. 85, Issue 11; pp. 921-932.
Giacomotto et al.; High-throughput Screening and Small Animal Models, Where Are We?; British Journal of Pharmacology; 2010; vol. 160, Issue 2; pp. 204-216.
Choudhury el al.; Fish and Chips: A Microfluidic Perfusion Platform for Monitoring Zebrafish Development; Lab on a Chip; 2012; vol. 12, Issue 5; pp. 892-900.
Chimote et al.; Comparison of Effects of Anti-angiogenic Agents in the Zebrafish Efficacy—Toxicity Model for Translational Anti-Angiogenic Drug Discovery; Drug Design, Development and Therapy; 2014; vol. 8; pp. 1107-1123.
Li et al.; Zebrafish on a Chip: A Novel Platform for Real-Time Monitoring of Drug-Induced Developmental Toxicity; PLoS One; 2014, vol. 9, Issue 4, e94792.
Crawford et al.; Zebrafish Bioassay-Guided Natural Product Discovery: Isolation of Angiogenesis Inhibitors from East African Medicinal Plants; PLoS One; 2011; vol. 6, Issue 2, e14694.
Wang et al.; Inhibitors of Neutrophil Recruitment Identified Using Transgenic Zebrafish to Screen a Natural Product Library; Disease Models & Mechanisms; 2014; vol. 7, Issue 1; pp. 163-169.
Kimmel et al.; Stages of Embryonic Development of the Zebrafish; Developmental Dynamics; 1995; vol. 203, Issue 3; pp. 253-310.
Duan et al.; Multi-Organ Toxicity Induced by Fine Particulate Matter PM2.5 in Zebrafish (*Danio rerio*) Model; Chemosphere; 2017; vol. 180; pp. 24-32.
Pan et al.; High-Sensitivity Real-Time Analysis of Nanoparticle Toxicity in Green Fluorescent Protein-Expressing Zebrafish; Small; 2013; vol. 9, Issue 6; pp. 863-869.
Brown et al.; Advances in the Study of Heart Development and Disease Using Zebrafish; Journal of Cardiovascular Development and Disease; 2016; vol. 3, Issue 2.
Stainier et al.; Cardiovascular Development in the Zebrafish. I. Myocardial Fate Map and Heart Tube Formation; Development; 1993; vol. 119 , Issue 1; pp. 31-40.
Nguyen et al.; Zebrafish as a Model for Cardiovascular Development and Disease; Drug Discovery Today: Disease Models; 2008; vol. 5, Issue 3; pp. 135-140.
Keßler et al.; Recent Progress in the Use of Zebrafish for Novel Cardiac Drug Discovery; Expert Opinion on Drug Discovery; 2015; vol. 10, Issue 11; pp. 1231-1241.
Howe et al.; The Zebrafish Model Organism Database: New Support for Human Disease Models, Mutation Details, Gene Expression Phenotypes and Searching; Nucleic Acids Research; 2016; vol. 45; D758-D768.
Lin et al.; Zebrafish High-Throughput Screening to Study the Impact of Dissolvable Metal Oxide Nanoparticles on the Hatching Enzyme, ZHE1; Small; 2013; vol. 9, Issue 9-10; pp. 1776-1785.
Chan et al.; Noninvasive Technique for Measurement of Heartbeat Regularity in Zebrafish (*Danio rerio*) Embryos; BMC Biotechnology; 2009; vol. 9:11.
Yang et al.; Fish-on-a-Chip: Microlluidics for Zebrafish Research; Lab on a Chip; 2016; vol. 16, Issue 7; pp. 1106-1125.
Hou et al.; Cardiac Output and Peripheral Resistance during Larval Development in the Anuran Amphibian Xenopus Laevis; American Journal of Physiology—Regulatory, Integrative and Comparative Physiology; 1995; vol. 269, Issue 5; R1126-R1132.
Chen et al.; Developmental and Organ-Specific Toxicity of Cucurbit[7]uril: In Vivo Study on Zebrafish Models; RSC Advances; 2015; vol. 5, Issue 38; pp. 30067-30074.
Nair et al.; Ultrasonography Reveals In Vivo Dose-Dependent Inhibition of End Systolic and Diastolic Volumes, Heart Rate and Cardiac Output by Nesfatin-1 in Zebrafish; General and Comparative Endocrinology; 2016; vol. 234; pp. 142-150.
Wielhouwer et al.; Zebrafish Embryo Development in a Microfluidic Flow-Through System; Lab on a Chip; 2011; vol. 11, Issue 10; pp. 1815-1824.
Dertinger et al.; Generation of Gradients Having Complex Shapes Using Microfluidic Networks; Analytical Chemistry; 2001; vol. 73, Issue 6; pp. 1240-1246.
Jeon et al.; Generation of Solution and Surface Gradients Using Microfluidic Systems; Langmuir; 2000; vol. 16, Issue 22; pp. 8311-8316.
Yang et al.; An Integrated Microfluidic Array System for Evaluating Toxicity and Teratogenicity of Drugs on Embryonic Zebrafish Developmental Dynamics; Biomicrofluidics; 2011; vol. 5, Issue 2, 024115.
Chang et al.; Fully Automated Cellular-Resolution Vertebrate Screening Platform with Parallel Animal Processing; Lab on a Chip; 2012; vol. 12, Issue 4; pp. 711-716.
Pardo-Martin et al.; High-Throughput Hyperdimensional Vertebrate Phenotyping; Nature Communications; 2013; vol. 4: 1467.

(56) References Cited

OTHER PUBLICATIONS

Tamplin et al,; A Platform for Automated Screening of Zebrafish Larvae in High Throughput Should Allow Detection of Phenotypic Changes in Single Cells; Nature Methods; 2010; vol. 7, Issue 8; pp. 600-601.

Pardo-Martin et al.; High-Throughput In Vivo Vertebrate Screening; Nature Methods; 2010; vol. 7, Issue 8; pp. 634-638.

Hong et al.; A Novel Long-Term, Multi-Channel and Non-Invasive Electrophysiology Platform for Zebrafish; Science Reports; 2016; vol. 6: 28248.

Bischel et al.; Zebrafish Entrapment by Restriction Array (ZEBRA) Device: A Low-Cost, Agarose-Free Zebrafish Mounting Technique for Automated Imaging; Lab on a Chip; 2013; vol. 13, Issue 9; pp. 1732-1736.

Lin et al.; High-Throughput Mapping of Brain-Wide Activity in Awake and Drug-Responsive Vertebrates; Lab on a Chip; 2015; vol. 15, Issue 3; pp. 680-689.

Yang et al.; Cell Docking and On-Chip Monitoring of Cellular Reactions with a Controlled Concentration Gradient on a Microfluidic Device; Analytical Chemistry; 2002; vol. 74, Issue 16; pp. 3991-4001.

Toepke et al.; PDMS Absorption of Small Molecules and Consequences in Microfluidic Applications; Lab on a Chip; 2006; vol. 6, Issue 12; pp. 1484-1486.

Vickers et al.; Generation of Hydrophilic Poly(dimethylsiloxane) for High-Performance Microchip Electrophoresis; Analytical Chemistry; 2006; vol. 78, Issue 21; pp. 7446-7452.

Akagi et al.; Miniaturized Embryo Array for Automated Trapping, Immobilization and Microperfusion of Zebrafish Embryos; PLoS One; 2012; vol. 7, Issue 5, e36630.

Akagi et al.; Fish on Chips: Microfluidic Living Embryo Arrays for Accelerated In Vivo Angiogenesis Assays; Sensors and Actuators B: Chemical; 2013; vol. 189; pp. 11-20.

Zhu et al.; Real-Time 2D Visualization of Metabolic Activities in Zebrafish Embryos Using a Microfluidic Technology; Cytometry Part A; 2015; vol. 87, Issue 5; pp. 446-450.

Judenherc-Haouzi et al.; Methylene Blue Counteracts H2S Toxicity-Induced Cardiac Depression by Restoring L-Type Ca Channel Activity; American Journal of Physiology. Regulatory, Integrative and Comparative Physiology; 2016; vol. 310, Issue 11; R1030-R1044.

Echevarria et al.; Methylene Blue Facilitates Memory Retention in Zebrafish in a Dose-Dependent Manner; Zebrafish; 2016; vol. 13, Issue 6; pp. 489-494.

Costa et al.; Methylene blue toxicity in zebrafish cell line is dependent on light exposure; Cell Biology International; 2016; vol. 40, Issue 8; pp. 895-905.

Candelier et al.; A Microfluidic Device to Study Neuronal and Motor Responses to Acute Chemical Stimuli in Zebrafish; Science Reports; 2015; vol. 5: 12196.

Lipshultz et al.; Treatment-Related Cardiotoxicity in Survivors of Childhood Cancer; Nature Reviews Clinical Oncology; 2013; vol. 10, Issue 12; pp. 697-710.

Xi; Visnagin—A New Protectant against Doxorubicin Cardiotoxicity? Inhibition of Mitochondrial Malate Dehydrogenase 2 (MDH2) and Beyond; Annals of Translational Medicine; 2016; vol. 4, Issue 4: 65.

Liu et al.; Visnagin Protects against Doxorubicin-Induced Cardiomyopathy through Modulation of Mitochondrial Malate Dehydrogenase; Science Translational Medicine; 2014; vol. 6, Issue 266, 266ra170.

Beis et al.; Genetic and Cellular Analyses of Zebrafish Atrioventricular Cushion and Valve Development; Development; 2005; vol. 132, Issue 18; pp. 4193-4204.

Scherz et al.; High-Speed Imaging of Developing Heart Valves Reveals Interplay of Morphogenesis and Function; Development; 2008; vol. 135, Issue 6; pp. 1179-1187.

Timmerman et al.; Notch Promotes Epithelial-Mesenchymal Transition during Cardiac Development and Oncogenic Transformation; Genes & Development; 2004; vol. 18, Issue 1; pp. 99-115.

Yalcin et al.; Heart Function and Hemodynamic Analysis for Zebrafish Embryos; Developmental Dynamics; 2017; vol. 246, Issue 11; pp. 868-880.

Westerfield; The Zebrafish Book. A Guide for the Laboratory Use of Zebrafish (*Danio rerio*); 4th edition; University of Oregon Press, Eugene; 2000; https://zfin.org/zf_info/zfbook/zfbk.html.

\* cited by examiner

MICROFLUIDIC SCREENING SYSTEM

CROSS-REFERENCE TO RELATED APPLICATIONS

The present application claims priority to and the benefit of U.S. Provisional Patent Application Ser. No. 62/419,489, entitled MICROFLUIDIC BASED LARGE-SCALE FISH SCREENING SYSTEM, which was filed on Nov. 9, 2016, and is hereby incorporated by reference in its entity.

FIELD OF THE INVENTION

The present disclosure generally relates to a microfluidic device and system and methods for using the same, and in particular, to a microfluidic device, system and methods useful for, e.g., large-scale fish screening.

BACKGROUND OF THE INVENTION

High throughput screening of experimental drugs is conventionally used for drug discovery and addressing biological questions that are otherwise unfeasible using other approaches. Among a variety of small organism experimental models, zebrafish (*Damio rerio*), with conserved key developmental processes across all vertebrates, is one of the best vertebrate models to study complex developmental processes and to conduct drug assessment assays. Zebrafish have distinct advantages over other vertebrate models. For example, zebrafish are easy to maintain, simple to administer drugs, and have a short reproductive cycle. The embryos/larvae of zebrafish are transparent, allowing the visual inspection of developing cells and organs within the embryos/larvae. The zebrafish heart utilizes similar molecular strategies and involves similar morphogenetic processes to a human heart, making the transparent zebrafish a valuable model for investigating the molecular basis of heart development, as well as for assessing the therapeutic potential of small molecules. Therefore, zebrafish and its embryo/larvae models provide efficient and low-cost substitute for conventional mouse assays, and are ideal models for large-scale drug screening.

Routine zebrafish experiments require anesthetized zebrafish to be manually positioned with a particular posture on agarose coated microplates or glass slides by skilled personnel. Such a conventional approach is time-consuming, and impractical to handle a large number of zebrafish simultaneously. In addition, this conventional zebrafish positioning approach may lead to abnormal conditions of zebrafish (e.g., anesthetized condition), and thus introduces substantial analytical bias. Another problem arising from the manual zebrafish positioning approach, which requires sacrificing of an individual larva at each time point, is that it is impossible to trace the time course responses of an individual larva. A further problem is that the manual positioning of an anesthetized zebrafish is not feasible for automated data acquisition using current microscopic techniques, as current microscopic techniques require each larva to be confined within a small area and kept in a certain posture, i.e. either dorsal or ventral orientation, to obtain a clear view for the tissue(s) of interest. Therefore, there is a need for an automated large-scale fish screening platform to manipulate these small-sized organisms with precise control.

SUMMARY OF THE INVENTION

Considering the whole life cycle of a zebrafish occurs in water, a microfluidic chip has the potential to yield a powerful tool for large-scale, automated zebrafish studies. Provided herein is a microfluidic chip that enables, e.g., scalable sample loading, parallel, long-term fish incubation, and/or automated fish observation/testing.

In a first aspect, a microfluidic based large-scale fish screening platform of the present disclosure is capable of loading a large amount of zebrafish larvae into designated positions of a microfluidic device. In the conventional technologies, no matter how many larvae a microfluidic chip can process, loading becomes the throughput bottleneck if it scales linearly with sample size. In addition, certain embryo loading strategies in the art may have fungal contamination problems arising from the remained eggshells once the larvae are hatched. Fungicide such as methylene blue is usually used to address contamination issues, which however undesirably induces potential chemical interactions and side effects on fragile larvae and thus may adversely interfere with drug screening results.

In a second aspect, a microfluidic based large-scale fish screening platform of the present disclosure is capable of achieving parallel and long-term incubation such that drug efficacy can be assessed throughout the developmental process of a zebrafish larva.

In a third aspect, a microfluidic based large-scale fish screening platform of the present disclosure has the capability to hold a large amount of zebrafish larvae at a particular posture for image acquisition. Although it may sound simple, imaging a large amount of freely moving larvae becomes a great technical challenge. In the conventional technologies, the movements of larvae along x, y and z axes suggest the need for plate scanning with a small field of view or sacrificing the magnification using a large field of view. It also poses another challenge to keep the swimming organisms in focus during video capture.

The aforementioned aspects are addressed by a microfluidic device or system of the present disclosure, which eliminate or diminish at least some of the disadvantages and problems described above.

In certain embodiments, the present disclosure relates to a microfluidic device, the device comprises an incubation layer, the incubation layer includes at least one dock, each of the at least one dock defines a stepped tank comprising an upper tank and a lower tank, an inflow channel in fluid communication with the stepped tank for supplying a fluid to the stepped tank, and an outflow channel in fluid communication with the stepped tank for draining the fluid from the stepped tank, wherein the geometry of the upper tank is configured to allow culturing of a fish larva therein, and wherein the geometry of the lower tank is configured to reversibly receive the fish larva from the upper tank and to dock the fish larva at a controlled orientation for imaging or observation.

In certain embodiments, the geometry of the lower tank fits the dimension of the fish larva so that the fish larva assumes a dorsal or ventral orientation when it is received in the lower tank.

In certain embodiments, the outflow channel is arranged above the inflow channel, optionally the inflow channel is in fluid communication with the lower tank, and the outflow channel is in fluid communication with the upper tank.

In certain embodiments, the lower tank has an inverted trapezoidal or a V shaped longitudinal cross-section.

In certain embodiments, the lower tank has a width of 0.3-0.5 mm.

In certain embodiments, the upper tank has a width of 0.8-0.9 mm.

In certain embodiments, the outflow channel is further configured to supply the fluid to the stepped tank.

In certain embodiments, the incubation layer comprises a plurality of functional series of docks, each of the plurality of functional series of docks comprises a plurality of docks and an inlet port in fluid communication with the inflow channels of the plurality of docks, and an outlet port in fluid communication with the outflow channels of the plurality of docks.

In certain embodiments, the microfluidic device further comprises a manifold layer, the manifold layer includes at least two inlets in fluid communication with at least two external fluid sources for receiving at least a first component and a second component of the fluid; a plurality of outlets, each of the plurality of outlets is in fluid communication with the port of a respective functional series of docks, and a manifold structure in fluid communication with the at least two inlets and the plurality of outlets.

In certain embodiments, the manifold structure comprises a gradient generator, the gradient generator is configured to receive the first component and the second component of the fluid from the at least two inlets and deliver to the plurality of outlets mixtures of the first component to the second component at various ratios.

In certain embodiments, the manifold layer further comprises a flooding structure, the flooding structure has a plurality of branches, each of the plurality of branches is in fluid communication with the gradient generator and a respective outlet of the plurality of outlets.

In certain embodiments, the microfluidic device further comprises a cover layer with a plurality of exits, each of the plurality of exits is in fluid communication with the outlet port of a respective functional series of docks.

In certain embodiments, a same fluidic resistance is achieved in each fluidic path between each of the at least two inlets of the manifold layer and a corresponding exit of the cover layer.

In certain embodiments, the at least two inlets of the manifold layer are in fluid communication with at least one inlet pump, the plurality of exits of the cover layer are in fluid communication with at least one outlet pump, and the at least one inlet pump and the at least one outlet pump can be operated at the same or different flow rates.

In certain embodiments, a 3-way valve can be in fluid communication with an exit of the cover layer, a respective outlet pump, and a medium reservoir.

In certain embodiments, the microfluidic device further comprising: a loading layer, the loading layer including: a plurality of stepped wells each in fluid communication with a respective dock, each of the plurality of stepped wells comprising an upper well and a lower well, wherein the geometry of the upper well is configured to accommodate a single embryo of a fish; wherein the geometry of the lower well is configured so that only the hatched larva of the embryo is capable of passing through the lower well from the upper well into the respective dock.

In certain embodiments, the upper well of each of the plurality of stepped wells has a hollow cylindrical shape with a diameter in the range from 1.46 mm to 1.96 mm, preferably 1.7±0.1 mm.

In certain embodiments, the lower well of each of the plurality of stepped wells has a hollow cylindrical shape with a diameter in the range from 0.4 mm to 0.6 mm.

In certain embodiments, the present disclosure relates to a drug screening assay using the aforementioned microfluidic device with a fish larva in each dock, wherein the assay comprising the steps of: a) draining the fluid from the stepped tanks to lower the water level below the upper tanks so that the fish larvae are docked in the lower tanks with a controlled orientation; b) imaging or observing the fish larvae for an observing period; c) flooding the fluid to the stepped tanks to leverage the water level above the lower tanks so that the fish larvae are released to the upper tanks for further culturing; and d) optionally repeating steps a) to c).

In certain embodiments, the present disclosure relates to a drug screening assay using the aforementioned microfluidic device, wherein the assay comprising the steps of: a) applying drops of fish embryos onto the loading layer; b) incubating the fish embryos in the stepped wells of the loading layer for a hatching period; c) hatching and spontaneously transferring the hatched larvae from the stepped wells of the loading layer to the stepped tanks of the incubation layer; d) removing the loading layer from the remaining part of the microfluidic device; e) draining the fluid from the stepped tanks to lower the water level below the upper tanks so that the fish larvae are docked in the lower tanks with a controlled orientation; f) imaging or observing the fish larvae for an observing period; g) flooding the fluid to the stepped tanks to leverage the water level above the lower tanks so that the fish larvae are released back to the upper tanks for further culturing; and h) optionally repeating steps e) to g).

In certain embodiment, the drug screening assay comprises between steps a) and b) a further step i) of washing away unloaded embryos with a medium.

DETAILED DESCRIPTION OF THE INVENTION

Figure 1:
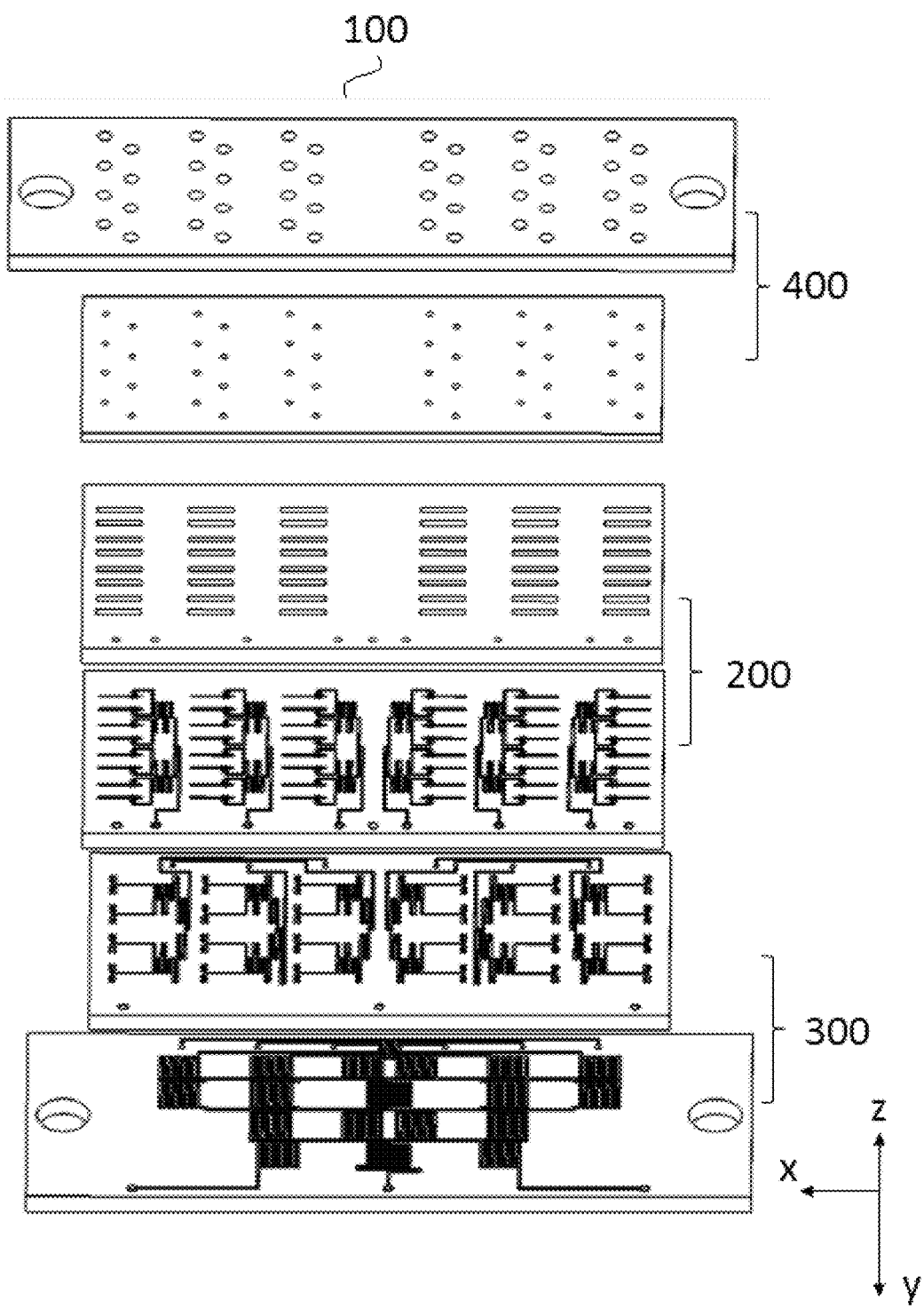
FIG. 1 illustrates a microfluidic device according to certain embodiments of the present disclosure.

For the purposes of the present disclosure, zebrafish embryo and zebrafish larva are described in connection with the microfluidic device, the large-scale screening system and the methods thereof described herein only as exemplary embodiments. It should be appreciated that the uses of the device, system and methods are not limited to zebrafish, but also other types of fish including but not limited to medaka (*Oryzias latipes*), antarctic fish (suborder Notothenioidei), Mexican tetras (*Astyanax mexicanus*), toadfish (Batrachoididae), bicolor damselfish (*Stegastes partitus*) and platyfish (*Xiphophorus maculatus*), and other types of living organs including but not limited to *Caenorhabditis elegans* and three-dimensional (3D) multicellular spheroids. It should be further appreciated that the uses of the device, system and methods are not limited to screen drugs. It will be understood that, in light of the present disclosure, the microfluidic device, the large-scale screening system and the methods thereof can also be successfully used, for example, for screening other substances including but not limited to toxics and poisons.

The term "drug" throughout the present disclosure, unless the context indicates otherwise, refers to any chemical or biological substance that is used to treat, cure, prevent or promote well-being of a living organism. Examples of drugs include chemicals, nucleic acids, proteins/enzymes and tagged antibodies.

Additionally, to assist in the description of the structural configuration, words such as length, width, height, depth, upper, lower, top, bottom, longitudinal, horizontal and the like are used. Unless their contextual usage indicates otherwise, these words are to be understood herein as having no structural, functional or operational significance and as merely reflecting the arbitrarily chosen orientation. When a dimension, such as width, is used with a cross-section the dimension of which is varying, the dimension can refer to the largest value or the average value of the cross-section. For instance, if the cross-section is a V shape, the width of the cross-section can refer to the largest width between the two ends of the V shape or half of the largest width. If the cross-section is a trapezoidal shape, the width of the cross-section can refer to the width of the largest base, or the average value of the width of the two parallel bases.

The term "layer" throughout the present disclosure, unless the context indicates otherwise, is not limited to a single layer structure. Where a layer is referred to, it can be a combination of multiple layers and components within the layer can be distributed in the multiple layers. Likewise, where multiple layers are referred to, they can be combined as a single layer and components within the multiple layers can be incorporated into the single layer. Where multiple layers are said to be stacked on each other, they can also be arranged in other manners, such as in a plane.

The term "in fluid communication" throughout the present disclosure, unless the context indicates otherwise, does not indicate a fluid must flow from one of the two components in fluid communication directly to the other. There can be one or more other components, such as devices, valves, ports, ducts, tubings, etc. between the two components.

Throughout the present disclosure, multiple pipeline components and opening components, such as channels, ducts, inlets, outlets, ports, branches, tubings, exits, entrances and apertures are used to enable fluid communication. It should be understood they are not necessarily distinct components, but some may share the same components and are named differently merely for the sake of ease of describing the structural configuration. For instance, where a channel is connected to a branch through a port, this may refer to one single channel, and vice versa. Unless the context indicates otherwise, the present disclosure is not meant to restrict how fluid is communicated from one structural element to another structural element.

Structural Configuration of the Microfluidic Device

FIG. 1 illustrates a microfluidic device 100 according to certain embodiments of the present disclosure in a space defined by an x-y-z coordinate system, where the x axis represents the length direction, the y axis represents the width direction, and z axis represents the height or depth or vertical direction. The microfluidic device 100 is in the form of a microfluidic chip and can be used as a lab on a chip (LOC). The microfluidic device 100 comprises one or more layers 200, 300, 400 stacked along the height direction. In certain embodiments, the microfluidic device 100 has a horizontal cross-sectional dimension of 25×60 mm in the x-y plane, but the dimension can be different according to practical needs, such as the capacity of the microfluidic device 100 and the size of the handling apparatus accommodating a plurality of the microfluidic devices 100. Therefore, any other reasonable dimensions of the microfluidic device 100 are also within the contemplation of the present disclosure.

Figure 2:
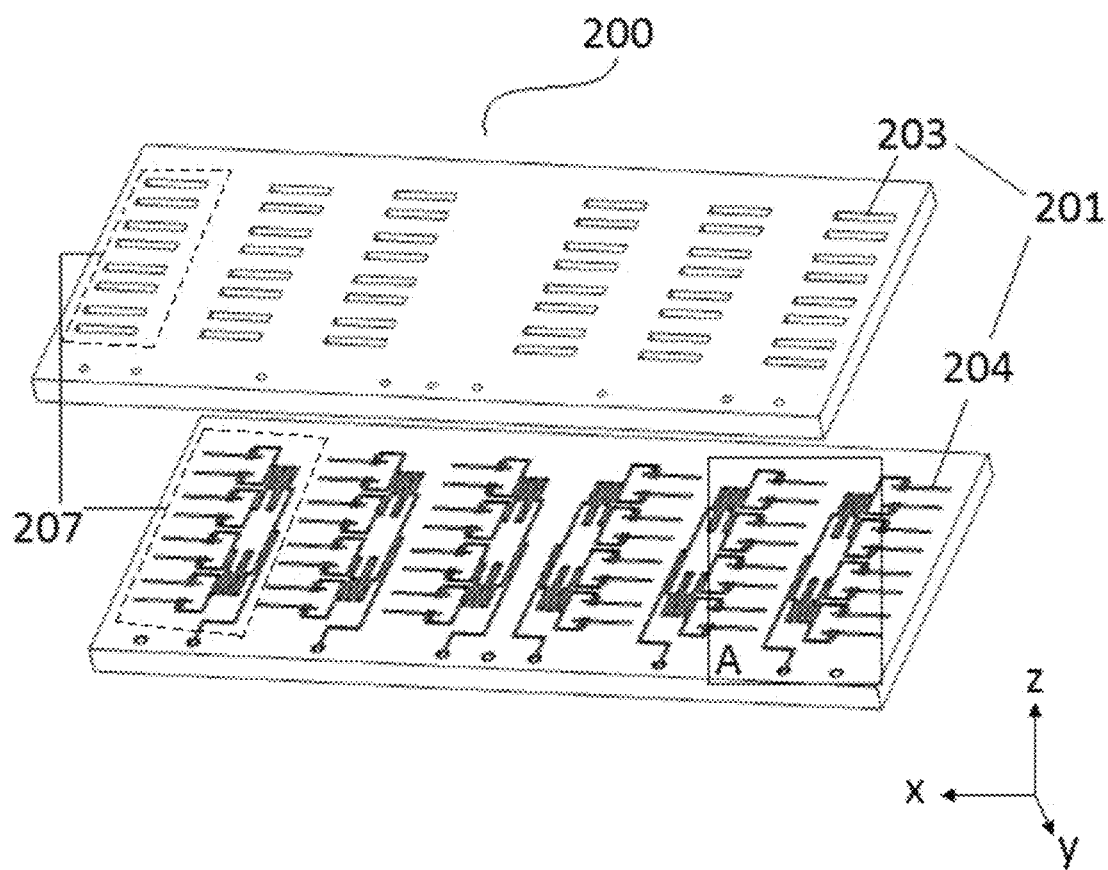
FIG. 2 illustrates an incubation layer according to certain embodiments of the present disclosure.

In certain embodiments, the microfluidic device 100 comprises an incubation layer 200. As shown in FIG. 2, the incubation layer 200 includes at least one dock 201. However, to achieve large-scale screening, a plurality of docks 201 can be included in the incubation layer 200. For instance, in certain embodiments, the incubation layer 200 can comprise any number of 1 to 128 docks 201, such as 8 to 124, 12 to 120, 16 to 116, 20 to 112, 24 to 108, 28 to 104, 32 to 100, 36 to 96, 40 to 92, 44 to 88, 48 to 84, 52 to 80, 56 to 76, 52 to 72, 48 to 68, 52 to 64, or 56 to 60 docks. Other reasonable numbers of the docks 201 are also within the contemplation of the present disclosure. Each dock 201 is designed to accommodate one zebrafish larva.

Figure 3:
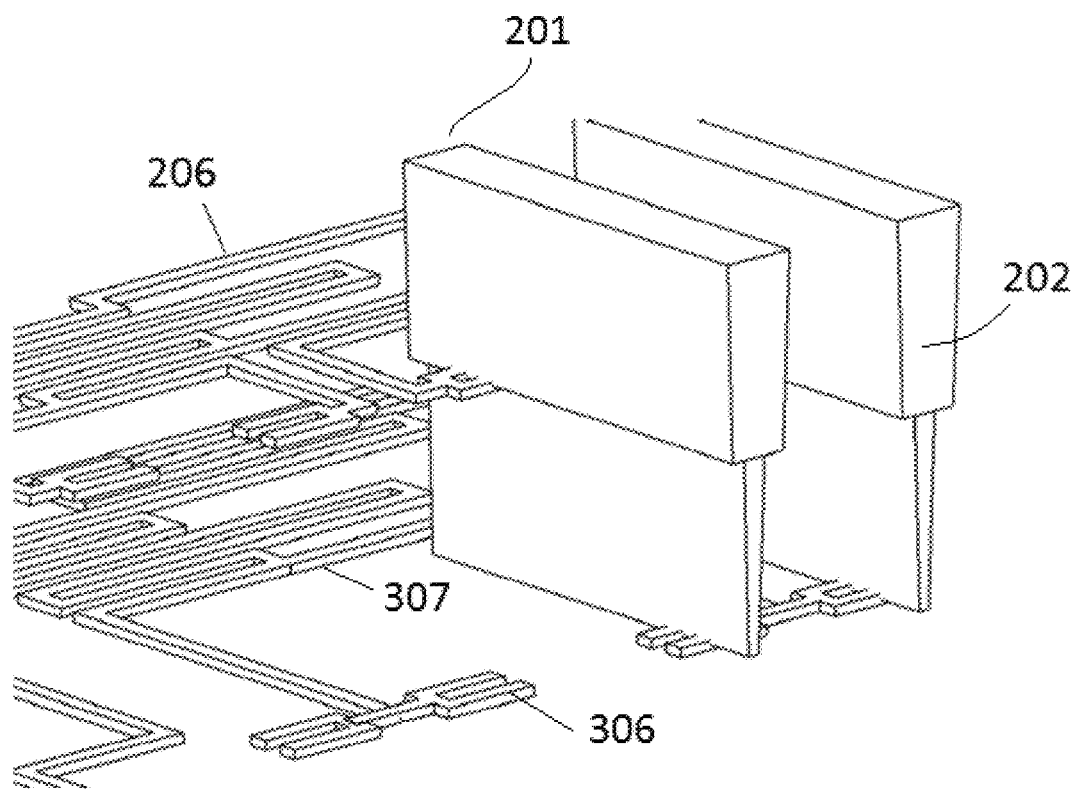
FIG. 3 illustrates two stepped tanks according to certain embodiments of the present disclosure, wherein certain stepped tanks are omitted for clarity.
Figure 4:
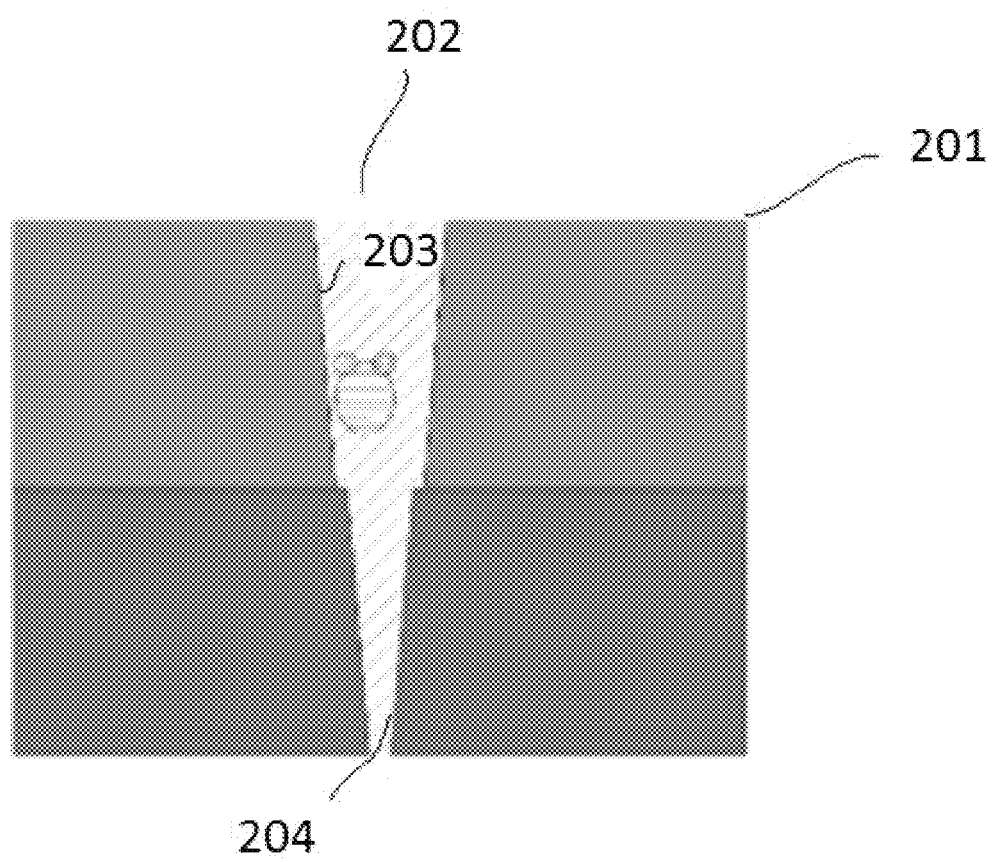
FIG. 4 illustrates a longitudinal cross-sectional shape in the y-z plane of the stepped tank according to certain embodiments of the present disclosure.

As shown in FIG. 3, the dock 201 defines a tank 202 with an upper opening, for instance to receive the zebrafish larva. The tank 202 has a stepped longitudinal cross-sectional shape in the y-z plane as shown in FIG. 4, dividing the tank 202 into an upper tank 203 and a lower tank 204. The upper tank 203 and the lower tank 204 are of different geometries. In certain embodiments, the upper tank 203 and/or the lower tank 204 can have a rectangular (FIG. 5A) or reversed trapezoidal or V-shape (FIG. 5B) longitudinal cross-section. In certain embodiments, the upper tank 203 and/or the lower tank 204 can have rectangular horizontal cross-section. The above cross-sectional shapes are convenient to fabricate using conventional Micro-Electro-Mechanical System (MEMS) processes, such as chemical etching or laser engraving, but other reasonable cross-sectional shapes are also possible and within the contemplation of the present disclosure. The upper tank 203 is generally larger than the lower tank 204.

Figure 6A:
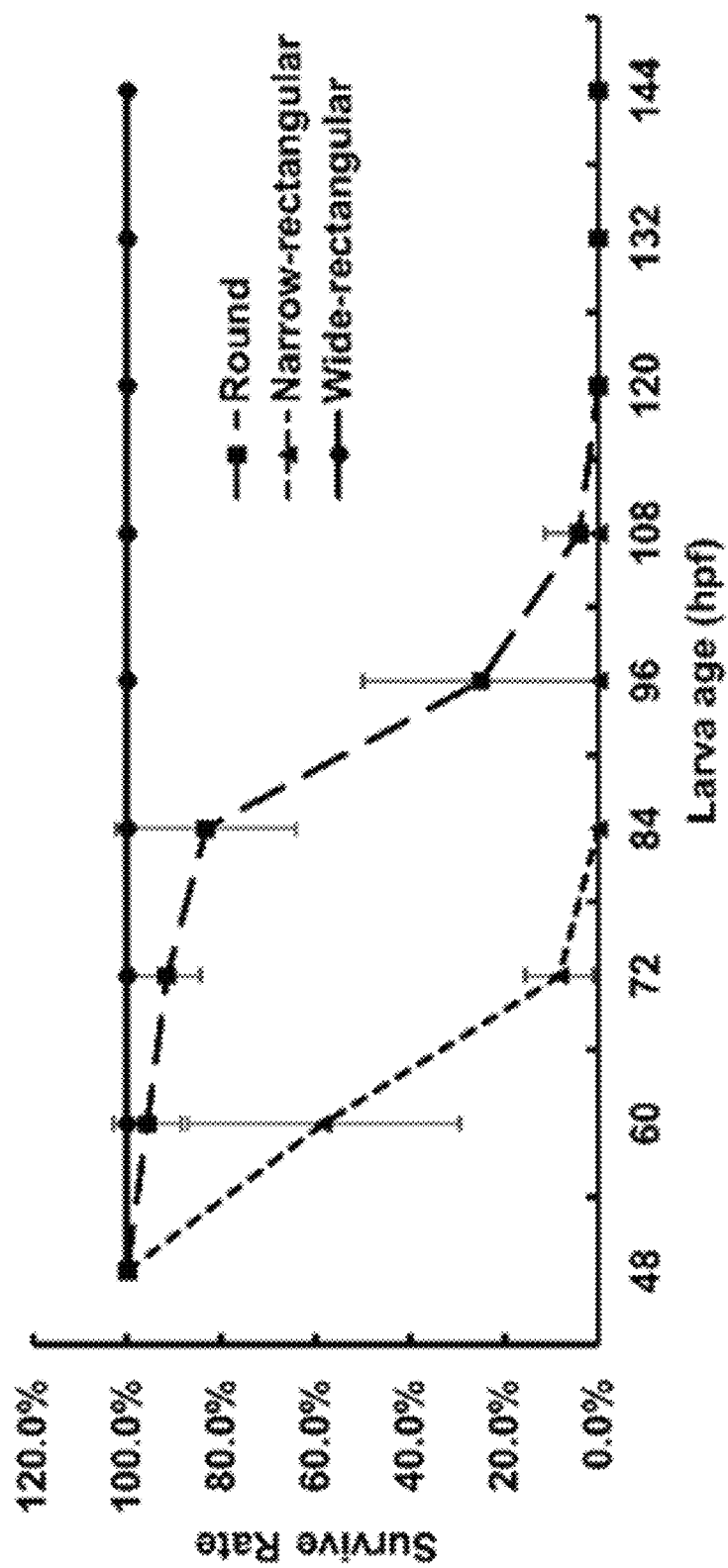
FIG. 6A shows the survival rate of zebrafish larvae cultured in round-shaped, narrow-rectangular, and wide-rectangular tanks according to certain embodiments of the present disclosure.
Figure 6B:
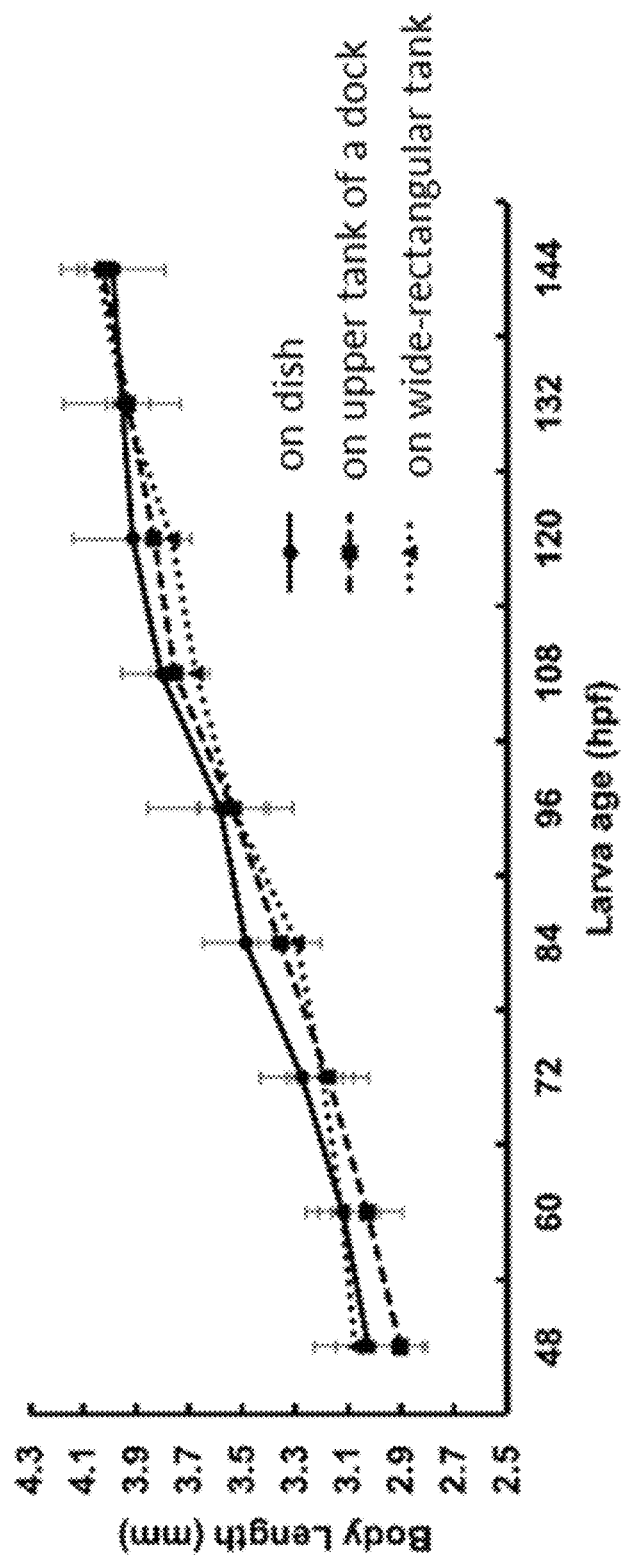
FIG. 6B shows the body length of zebrafish larvae cultured on a dish, on a wide-rectangular tank, and on an upper tank of a dock according to certain embodiments of the present disclosure.

The geometry of the upper tank 203 is configured to maintain viability of a zebrafish larva and to culture the zebrafish larva. For this purpose, the upper tank 203 is sized larger than the zebrafish larva. In certain embodiments, the size of the zebrafish larva is determined with reference to the largest dimension of zebrafish larvae, i.e., the average dimension of zebrafish larvae that are cultured for the longest hours in the assay or experiment. In certain embodiments, the zebrafish larva is cultured up to 144 hours post fertilization (hpf), up to 132 hpf, up to 120 hpf, up to 108 hpf, up to 96 hpf, up to 80 hpf, up to 68 hpf, or up to 56 hpf. In particular, the length of the upper tank 203 can be slightly larger than that of an ordinary zebrafish larva. The length of the upper tank 203 can be made even larger, but there is no particular benefit of it and it may unnecessarily enlarge the dimension of the chip. The depth of the upper tank 203 is not as important so long as it is larger than the height of the zebrafish larva. The width of the upper tank 203 can be substantially larger than that of an ordinary zebrafish larva, so that the zebrafish larva can swim freely in the upper tank 203. In certain embodiments, the upper tank 203 has a length between 1 to 9 mm, 2 to 8 mm, 3 to 7 mm, 4 to 6 mm, or 5 mm. In certain embodiments, the upper tank 203 has a length that is 5%-30%, 10%-25%, or 15%-20% longer than the length of the zebrafish larva. In certain embodiments, the upper tank 203 is 0.2 mm-1 mm, 0.3 mm-0.9 mm, 0.4 mm-0.8 mm, 0.5 mm-0.7 mm, or 0.6 mm longer than the length of the zebrafish larva. In certain embodiments, the upper tank 203 has a width between 0.5 mm-1.6 mm, 0.6 mm-1.5 mm, 0.7 mm-1.4 mm, 0.8 mm-1.3 mm, 0.85 mm-1.2 mm, 0.9 mm-1.1 mm or 1.0 mm. In certain embodiments, the upper tank 203 has a width that is 30%-100%, 40%-90%, 50%-80%, or 60%-70% larger than the width of the zebrafish larva. In certain embodiments, the upper tank 203 has a width that is 0.3 mm-1 mm, 0.4 mm-0.9 mm, 0.5 mm-0.8 mm, or 0.6 mm-0.7 mm wider than the width of the zebrafish larva. The width can be consistent or varying along the depth. In other words, the side walls can be tilted to define an angle of 0°-1°, 1°-9°, 2°-8°, 3°-7°, 4°-6°, or 5° relative to the vertical direction, In certain embodiments, the upper tank 203 has a depth between 1 to 3 mm, or 2 mm. It should be noted for other types of fish larvae or organisms, the same principle applies but different dimensions can be selected. In one embodiment, the upper tank 203 has a length of 5.0±0.03 mm and a width of 0.85±0.05 mm, and a depth of 2 mm. Experiments demonstrate that the survival rate of zebrafish larvae at 96 hpf in tanks with the same dimension of the upper tank 203 (wide-rectangular) is 100% (FIG. 6A) and no significant difference in terms of body length is observed when comparing the on-chip (in the upper tank) and off-chip (in a petri dish or a wide-rectangular tank) incubations of larvae originated from the same batch (FIG. 6B). By contrast, when cultured in a tank with a length of 9.5±0.06 mm and a width of 0.45±0.05 mm (narrow-rectangular), the larvae at 72 hpf have a survival rate of less than 10%, and the larvae at 96 hpf have a survival rate of zero (FIG. 6A). In a further experimental setup where the fish larvae are cultured in a round tank where the radius is 1.16±0.02 mm, the larvae at 96 hpf has a survival rate of about 20% (FIG. 6A).

Figure 5A:
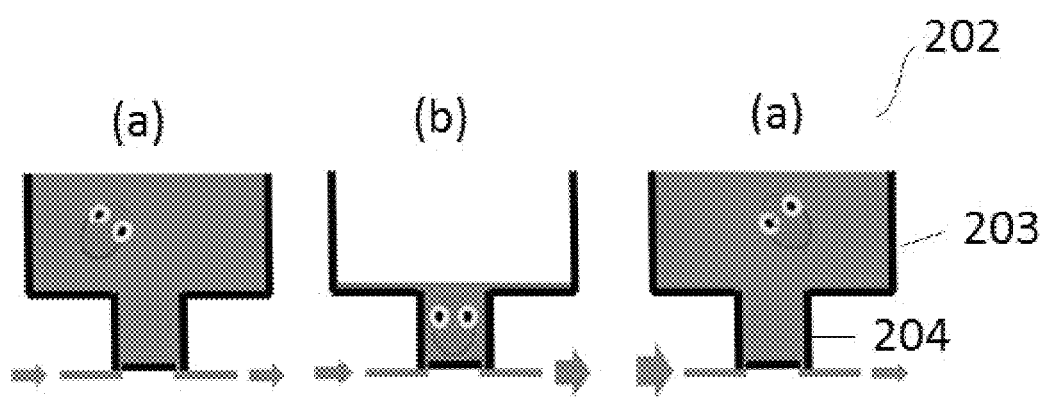
FIG. 5A illustrates (a) the releasing state and (b) the docking state of a tank with a rectangular longitudinal cross-section according to certain embodiments of the present disclosure.
Figure 5B:
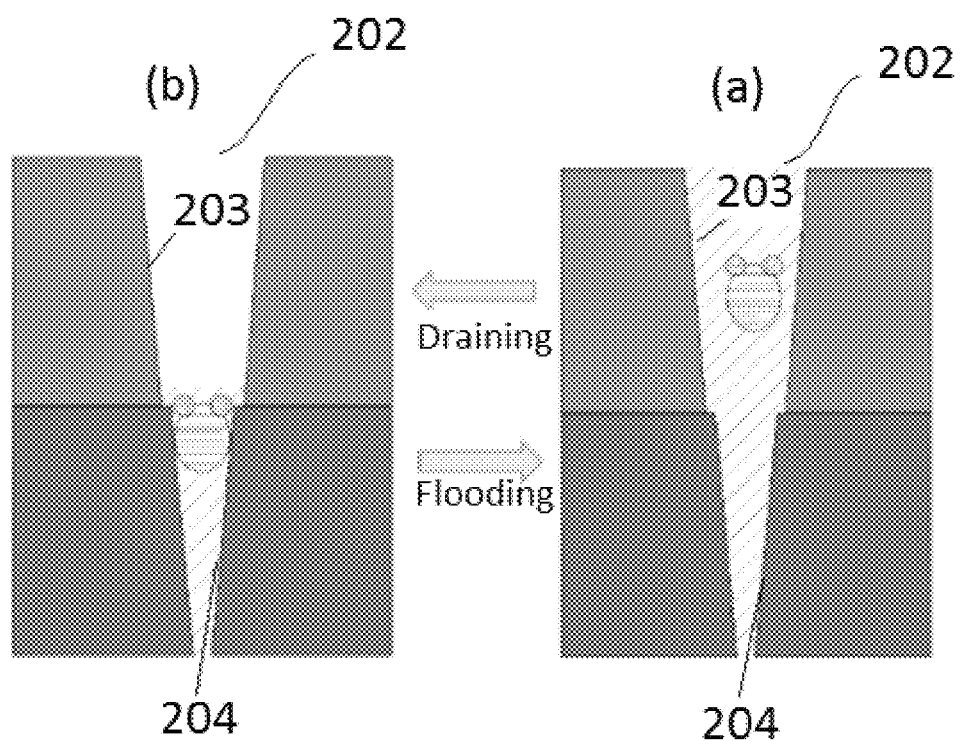
FIG. 5B illustrates (a) the releasing state and (b) the docking state of a tank with an inverted trapezoid, or a V shaped longitudinal cross-section according to certain embodiments of the present disclosure.

The geometry of the lower tank 204 is configured to reversibly receive the fish larva from the upper tank 203 and to hold the zebrafish larva at a controlled orientation for imaging and/or observation, as shown in FIG. 5A and FIG. 5B. The controlled orientation can be a dorsal or ventral orientation of the zebrafish larva. The dorsal orientation ("two-eye" posture) allows a clear imaging view of heart, cerebral vasculature and nervous system. For this purpose, the lower tank 204 is sized to fit the size of the zebrafish larva so that the zebrafish larva gets "docked" when it is received in the lower tank 204. In particular, the length can be slightly larger than that of an ordinary zebrafish larva. the depth can be slightly or substantially larger than that of an ordinary zebrafish. The width can be slightly larger than, the same as, or slightly smaller than that of an ordinary zebrafish. The width usually varies along the height so the lower tank 204 can receive a fish larva incubated for different hours post fertilization. In certain embodiments, the lower tank 204 has a length that is the same as the length of the upper tank 203. In certain embodiments, the lower tank 204 has a length between 1 to 9 mm, 2 to 8 mm, 3 to 7 mm, 4 to 6 mm, or 5 mm. In certain embodiments, the lower tank 204 has a length that is 5%-30%, 10%-25%, or 15%-20% longer than the length of the zebrafish larva. In certain embodiments, the lower tank 204 has a length that is 0.2 mm-1 mm, 0.3 mm-0.9 mm, 0.4 mm-0.8 mm, 0.5 mm-0.7 mm, or 0.6 mm longer than the length of the zebrafish larva. In certain embodiments, the lower tank 204 has a depth between 1 to 7 mm, 2 to 6 mm, 3 to 5 mm, or 4 mm. In certain embodiments, the lower tank 204 has a width between 0.1 to 0.5 mm, 0.2 to 0.4 mm, or 0.3 mm, or 0.45 mm. In certain embodiments, the lower tank 204 has a width that is 1%-10%, 2%-9%, 3%-8%, or 4%-7%, or 5%-6% smaller than the width of the zebrafish larva; or the lower tank 204 has a width that is 1%-10%, 2%-9%, 3%-8%, or 4%-7%, or 5%-6% larger than the width of the zebrafish larva. The width can be consistent or varying along the depth. In other words, the side walls can be tilted to define an angle of 0°-10°, 1°-9°, 2°-8°, 3°-7°, 4°-6°, or 5° relative to the vertical direction. An inverted trapezoidal or V-shape longitudinal cross-sectional shape with a sufficient depth of the lower tank 204 ensures the zebrafish larvae can be held at a controlled orientation for zebrafish larvae of different sizes at different incubation hours. It should be noted for other types of fish larvae or organisms, the same principles apply, but different dimensions can be selected. In one embodiment, the lower tank 204 has a width of 0.2 mm and a depth of 4 mm whereby the zebrafish larvae can be effectively orientated in a dorsal posture.

In certain embodiments, as shown in FIG. 3, an inflow channel (not shown) is in fluid communication with a stepped tank 202 for flooding a fluid to the stepped tank 202, and an outflow channel 206 in fluid communication with the stepped tank 202 for draining the fluid from the stepped tank 202, so that the stepped tank 202 can be filled with the fluid or drained for assay. The inflow channels and the outflow channels 206 can be in the same layer as the docks 201 or can extend to a different layer. In certain embodiments, both the outflow channel 206 and the inflow channel are connected to the stepped tank 202 at the bottom, as shown in FIG. 5A. In certain embodiments, the outflow channel 206 is arranged above the inflow channel, as shown in FIG. 3. This design minimizes the risk of over-draining the stepped tank 202 and trapping air bubbles during the flooding and draining process. In certain embodiments, the inflow channel is in fluid communication with the lower tank 204, and the outflow channel 206 is in fluid communication with the upper tank 203.

In certain embodiments, the inflow channel and the outflow channel 206, or the outflow channel 206 alone can also be used to control the water level in the stepped tank 202. FIG. 5A and FIG. 5B show (a) a release state and (b) a docking state. In the release state, both the upper tank 203 and the lower tank 204 of the stepped tank 202 are flooded with the fluid, such that a zebrafish larva can be cultured in the upper tank 203; while in the docking state, the fluid in the upper tank 203 has been drained and there is only fluid in the lower tank 204. The zebrafish larva falls into the lower tank 204 as a result of gravity and is held in a dorsal position for imaging or observation, as described above. After the imaging and/or observation, the upper tank 203 can be re-flooded with fluid so that the zebrafish larva can float up into the upper tank 203 and be cultured there again for the next imaging or observation. The process can be repeated many times with flooding and draining of the upper tank 203 and the zebrafish larva can be reversibly situated into the lower tank 204 and released therefrom.

Figure 7:
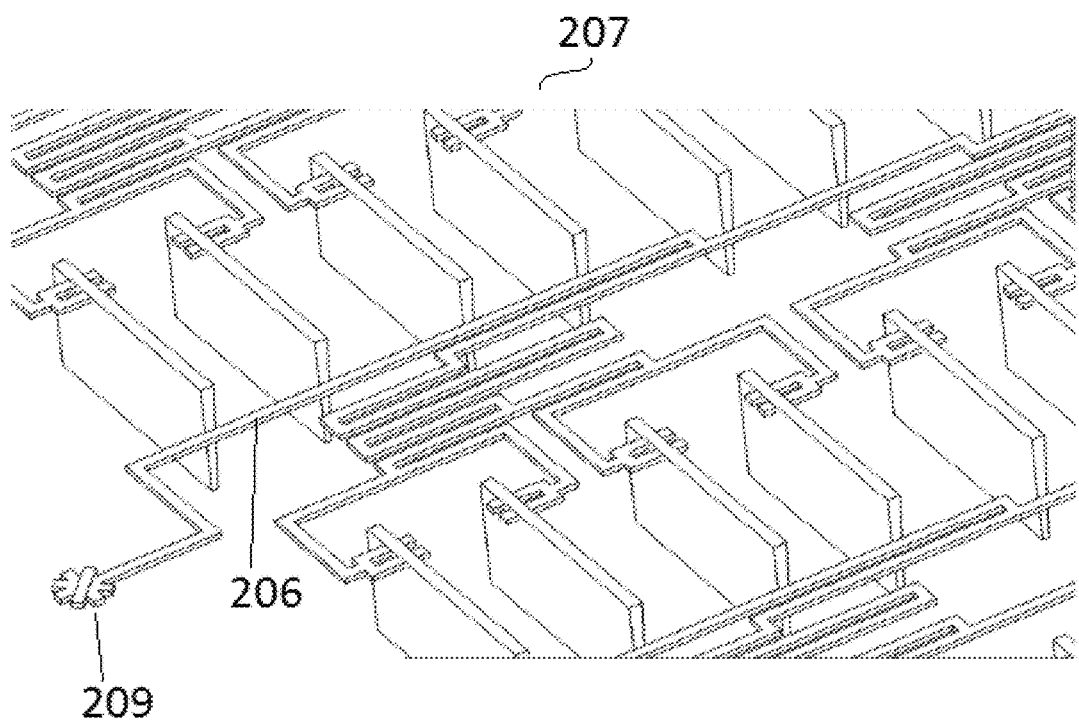
FIG. 7 is an enlarged view of the region A in FIG. 1, which illustrates lower tanks, an outlet port and associated channels of a functional series of docks according to certain embodiments of the present disclosure.

In certain embodiments, as shown in FIG. 2, the incubation layer 200 comprises a large number of docks 201 forming a plurality of functional series of docks 207, with each of the plurality functional series of docks 207 comprising a plurality of docks 201. Each functional series of docks 207 can be used for a respective experimental setup so that different experiments can be run simultaneously on the same fluid device 100. This significantly escalates the scale of assay. In certain embodiments, there are 48 docks 201, every 8 of them form a functional series 207 so there are 6 functional series of docks 207, as shown in FIG. 2. The 6 functional series of docks 207 are arranged parallel to each other along the length of the incubation layer 200. However, other configurations and arrangements of the functional series of docks 207 are also possible and within the contemplation of the present disclosure. In certain embodiments, each functional series of docks 207 comprises an inlet port (not shown) and an outlet port 209, as shown in FIG. 7. However, other quantities of inlet ports and outlet ports 209 for each functional series of docks 207 are also possible and within the contemplation of the present disclosure. The inlet port is in fluid communication with the inflow channels (not shown) of the plurality of docks 201 within the same functional series 207, so fluid can be received through the inlet port and distributed to the inflow channels and the tanks 202. The outlet port 209 is in fluid communication with the outlet flow channels 206 of the plurality of docks 201 in the same functional series 207, so fluid can be collected from the outflow channels 206 and the tanks 202, and discharged through the outlet port 209. In other embodiments, the inflow channels and the outflow channels 206 connect the docks 201 in series (therefore, inflow channels and outflow channels 206 can at least partly share the same channels) so that the inlet port connects to only one inflow channel and the outlet port 209 connects to only one outflow channel 206. Other ways of arranging the inlet port, the outlet port 209, the inflow channels and the outflow channels 206, whether in series, in parallel, or a combination thereof, are also possible and within the contemplation of the present disclosure. In certain embodiments, inlet ports and inflow channels are not provided. As shown in FIG. 3, the docks 201 can be in direct fluid communication with, for instance, branches 307 and outlets 306 of a manifold layer 300 to be described below. As such, the branches 307 and outlets 306 serve the function of inlet ports and inflow channels.

Figure 8:
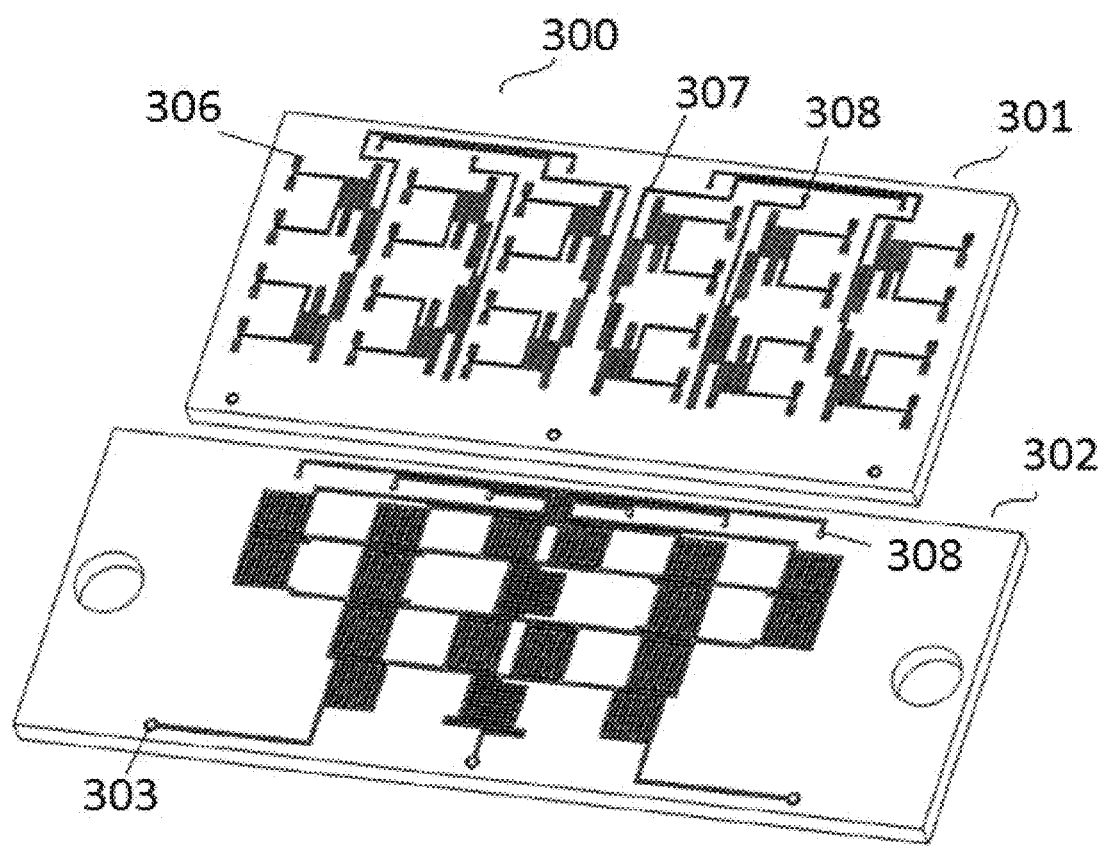
FIG. 8 illustrates a manifold layer according to certain embodiments of the present disclosure.

In certain embodiments, the microfluidic device 100 further comprises a manifold layer 300 as shown in FIG. 8. The manifold layer 300 receives fluid input from an external fluid apparatus (not shown), such as a fluid source, a fluid pump, or a syringe, and relays the fluid to the incubation layer 200. A manifold layer 300 is particularly useful where the incubation layer 200 comprises a large number of docks 201, as the manifold layer 300 receives fluid input at a macro scale and generates fluid output at a micro scale or mesoscopic scale, e.g., by a flooding structure 301 as described below. The manifold layer 300 can also receive multiple fluid inputs and produce multiple fluid outputs with different contents, e.g., by a gradient generator 302 as described below. The flooding structure 301 and the gradient generator 302 can be the same structure or they can be different structures. In certain embodiments, the manifold layer 300 includes two inlets 303 in fluid communication with two external fluid sources for receiving a first fluid (e.g., a drug or a first concentration of a drug) and a second fluid (e.g. a buffer, a medium, such as an E3 medium, or a second concentration of the drug). The manifold layer 300 is then capable of generating different fluid outputs with different ratios of the first fluid to the second fluid, as will be described below. Likewise, more than two inlets 303 can be provided if more than two fluids are needed. Alternatively, only one inlet 303 can be provided if only one fluid is needed. In certain embodiment, the manifold layer 300 includes a plurality of outlets 306, each of the plurality of outlets 306 is in fluid communication with an inlet port of a respective functional series of docks 207, or with a dock of a respective functional series of docks 207. As such, different fluid outputs with different ratios of the first fluid to the second fluid can be delivered to the inlet ports or docks 207 of different functional series of docks 207.

In certain embodiments, as shown in FIG. 8, the manifold structure 300 comprises a gradient generator 302. The gradient generator 302 comprises the inlets 303 and is configured to receive, for instance, the first fluid and the second fluid from the inlets 303 and generate outputs 308 with various ratios of the first fluid to the second fluid. In certain embodiments, the gradient generator 302 comprises a first number of ducts branching from a first group of one or more inlets 303 receiving the first fluid and a second number of ducts branching from a second group of one or more inlets 303 receiving the second fluid. Different numbers of ducts receiving the first fluid and ducts receiving the second fluid are then combined to produce fluid outputs 308 with different ratios of first fluid to second fluid. For instance, where three of the ducts receiving the first fluid are combined with two of the ducts receiving the second fluid, assuming the flow rate in each duct is identical, the output will have a ratio of 3:2 of the first fluid to the second fluid. In other words, the first fluid is diluted by 40%. With such arrangement, a concentration of the first fluid in the combined first and second fluid between 0% to 100% can be achieved. In certain embodiments, to improve the mixing, laminar flow and diffusive mixing within a duct is used. Other ways of mixing the first and second fluid are also possible and within the contemplation of the present disclosure. For instance, there can be three inlets 303 receiving a first concentration of a first fluid, a second concentration of the first fluid, and a second fluid, and various ducts are branching from the three inlets 303 combining. This can provide more flexibility in obtaining combined fluid with different contents. In certain embodiments, the ducts also function as a flooding structure 301 to convert the fluid flow from a macro scale to a micro or mesoscopic scale.

In certain embodiments, fluorescent dyes Resorufin (213 g mol$^{-1}$) and R110 (367 g mol$^{-1}$) are chosen to test the gradient generator 302 because of their availability and comparable molecular weight with target drug DPU (212 g mol$^{-1}$). With an infuse rate of 46 µL·h$^{-1}$ applied to all inlets 303, the experimental gradient profiles for Resorufin and R110 are reasonably aligned with the theoretical values of the gradient generator design.

In certain embodiments, as shown in FIG. 8, the manifold layer 300 further comprises a separate flooding structure 301. The flooding structure 301 comprises the outlets 306, receives fluid input 308 from the gradient generator 302 and converts the fluid input 308 from a macro scale to a micro or mesoscopic scale. The flooding structure 301 has a plurality of branches 307, each of the plurality of branches 307 is in fluid communication with the gradient generator 302 and a respective outlet 306.

In certain embodiments, the gradient generator 302 and the flooding structure 301 can be configured as two components in one layer or as two components in two distinct layers. Alternatively, the gradient generator 302 and the flooding structure 301 can be an integral component so gradient generation and scale conversion can be performed by one single component. For instance, the gradient generator 302 and/or the flooding structure 301 can have a Christmas tree structure.

Figure 9:
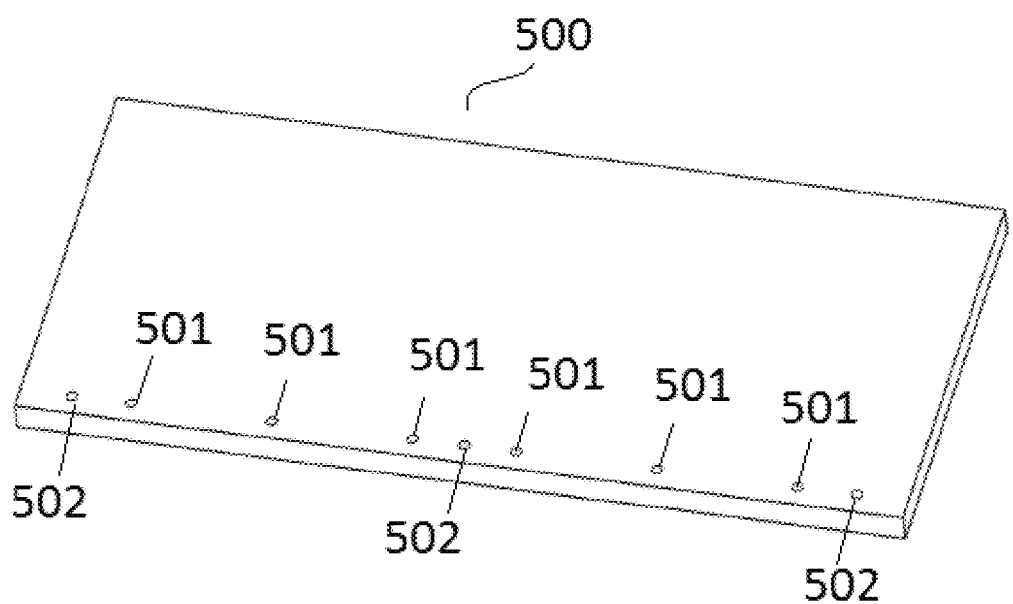
FIG. 9 illustrates a cover layer according to certain embodiments of the present disclosure.

In certain embodiments, the microfluidic device 100 further comprises a cover layer 500 as shown in FIG. 9. The cover layer 500 is stacked onto the incubation layer 200 as shown in FIG. 1 to protect the zebrafish larvae in the docks 201 from, e.g., unwanted environmental contaminants and to minimize evaporation or loss in any other undesired manners of the fluid in the docks 201. The cover layer 500 comprises a plurality of exits 501 and entrances 502, each of the plurality of exits 501 is in fluid communication with an outlet port 209 of a respective functional series of docks 207. The exits 501 are then connected to an external fluid apparatus (not shown), such as a fluid source, a fluid reservoir, a fluid pump, or a syringe. The entrances 502 are in alignment with inlets 303 of the manifold layer 300. Any layers between the cover layer 500 and the manifold layer 300 are provided with similar apertures to facilitate fluid communication between the entrances 502 and the inlets 303. However, a cover layer 500 is not essential. The outlet ports 209 of the incubation layer 200 can be directly connected to the external fluid apparatus without the cover layer 500.

In certain embodiments, a similar fluidic resistance is achieved in each fluidic path from an inlet 303 of the manifold layer 300 to a corresponding dock 201, from a dock 201 to a corresponding exit 501 of the cover layer 500, and/or between an inlet 303 of the manifold layer 300 and a corresponding exit 501 of the cover layer 500. The fluidic resistance is caused by the friction and other forces between the fluid and the duct through which the fluid flows. The fluidic resistance is affected by a number of factors, such as the material and diameter of the duct, the properties of the fluid and many other factors. With a similar fluidic resistance of different fluidic paths, the gradient generation, and the flooding and draining of the docks can be accurately controlled by simply resorting to the external fluid apparatus without addressing the divergences among different fluid paths in the microfluidic device 100. Therefore, the flow rate of the fluid and resulting exposure of the contents therein to the zebrafish can be more easily controlled.

Figure 10:
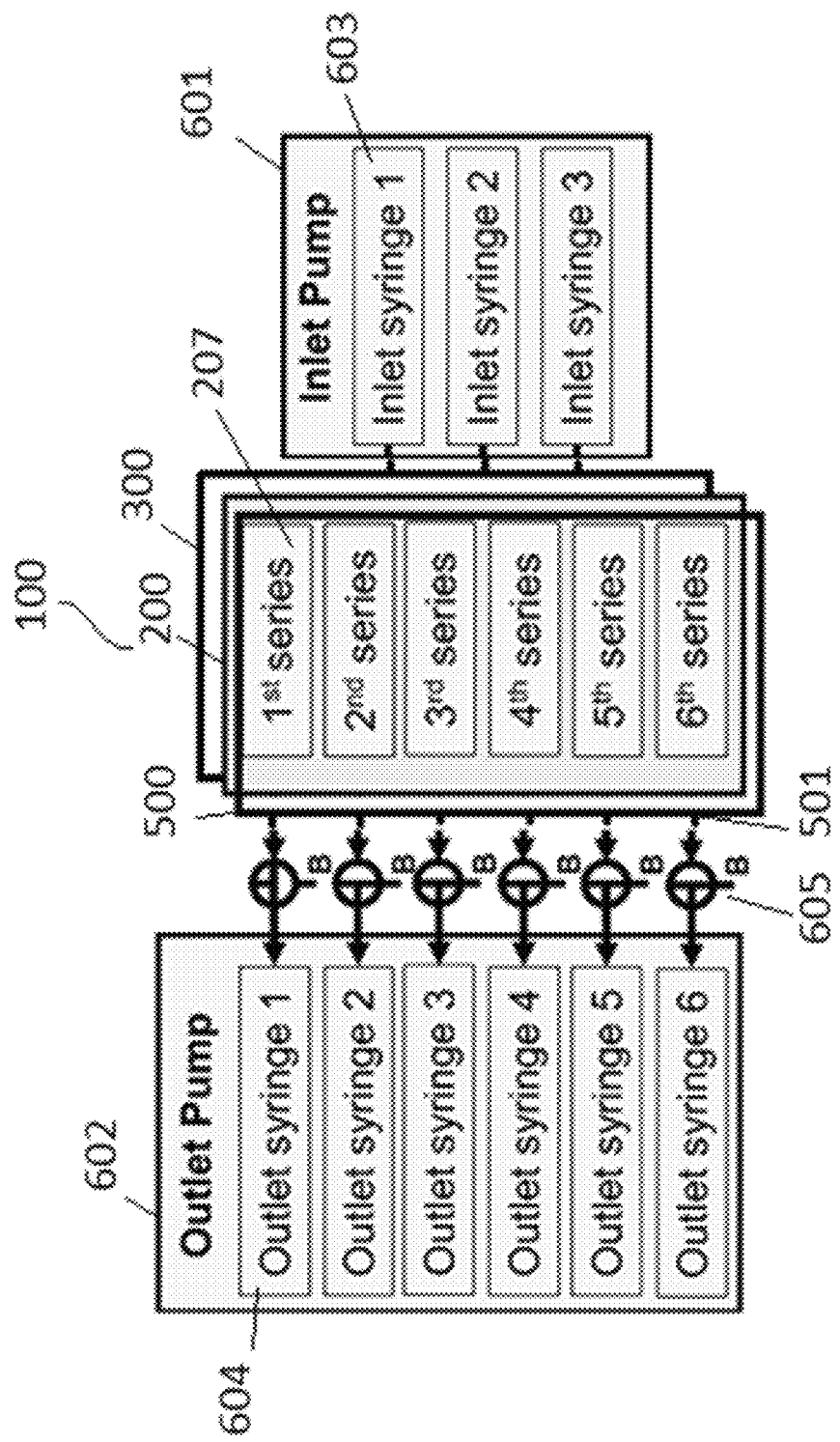
FIG. 10 illustrates the connections between the microfluidic device and the outlet pump, and between the microfluidic device and the inlet pump according to certain embodiments of the present disclosure.

In certain embodiments, the inlets 303 of the manifold layers 300 or the entrances 502 of the cover layer 500 are in fluid communication with at least one inlet pump 601 as shown in FIG. 10, so fluid input can be driven into the microfluidic device 100, the exits 501 of the cover layer 500 or the outlet port 209 are in fluid communication with at least one outlet pump 602 so fluid can be discharged from the microfluidic device 100. The at least one inlet pump 601 and the at least one outlet pump 602 can be switched on or off, or operated at the same or different flow rates so the fluid in the docks 201 can be circulated, flooded or drained, as described above. The at least one inlet pump 601 and/or the at least one outlet pump 602 can also be operated such that the fluid flow for each functional series of docks 207 can be controlled independently and differently. In certain embodiments, there is only one inlet pump 601 and only one outlet pump 602. The inlet pump 601 is used to fill one or more inlet syringes 603 in fluid communication with the inlets 303 of the manifold layers 300; each outlet pump 602 is used to fill or extract one or more outlet syringes 604 in fluid communication with the exits 501 of the cover layer 500. As such, the fluid flow for each functional series of docks 207 can be controlled independently by the corresponding inlet syringe 603 and/or the outlet syringe 604.

In certain embodiments, the at least one outlet pump 602 can serve as a draining pump as well as a flooding pump. As shown in FIG. 10, a 3-way valve 605 can be provided between an outlet pump 602 and a corresponding exit 501 of the cover layer 500. The 3-way valve 605 can be further in fluid communication with a medium reservoir B (not shown). The various medium reservoirs B indicated in FIG. 10 can be the same or different, depending on the medium used for each functional series is the same or different. When the outlet pump 602 works as a draining pump, the 3-way valve 605 is configured to first connect the syringe and chip, such that fluid can be drained from the corresponding dock(s) 201 by the outlet pump 602; and then to connect the syringe and the medium reservoir, such that fluid in the syringes can be discharged to the medium reservoir. When the outlet pump 602 works as a flooding pump, the 3-way valve 605 is configured to first connect the syringe and the medium reservoir, such that a medium from the medium reservoir can fill the syringe; and then to connect the syringe and the chip, such that fluid can be flooded into the corresponding dock(s) 201. As such, the outlet pump 602 (i.e., without the need of the inlet pump 601), together with the 3-way valve 605, the outflow channels 206 (i.e., without the need of the inflow channels), and the outlet ports 209 (i.e. without the need of the inlet ports) can flood and drain the docks 201. The inlet pump 601, the inflow channels (if present), and the inlet ports (if present) are still needed for administering drugs, but they are not essential in the flooding and draining process. Alternatively, the outlet pump 602, the 3-way valve 605, the outflow channels 206 and the outlet ports 209 provide extra flexibility to achieve water-level control in the docks 201 if not completely replacing the function of the inlet pump 601, the inflow channels (if present) and the inlet ports (if present) in flooding the docks 201.

Figure 11:
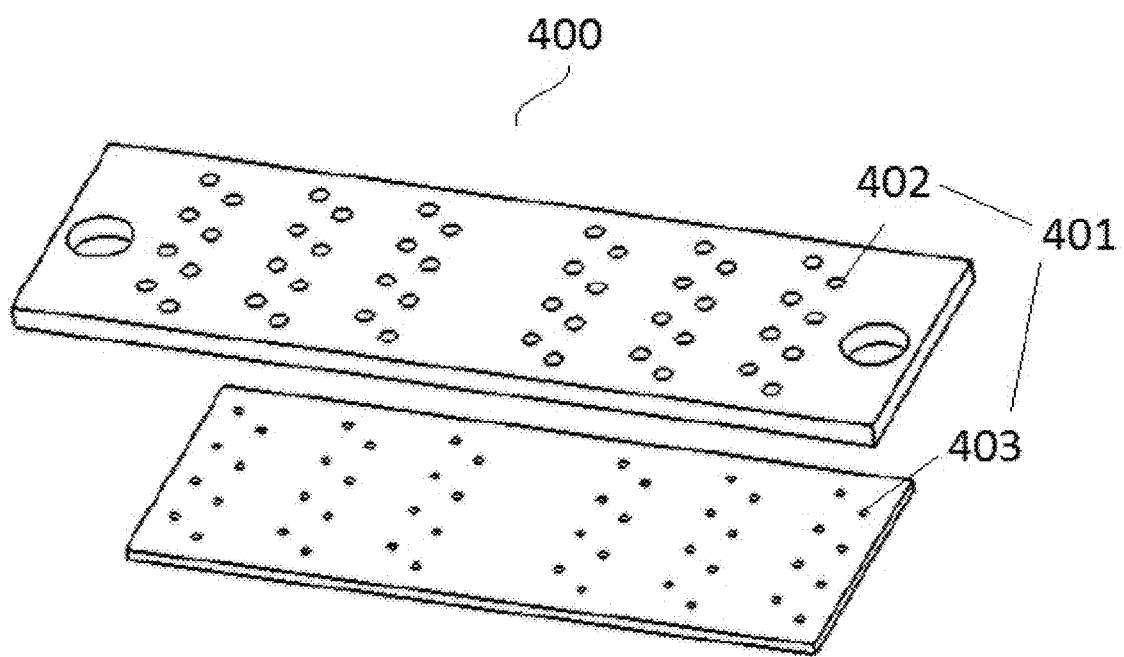
FIG. 11 illustrates a loading layer according to certain embodiments of the present disclosure.
Figure 12:
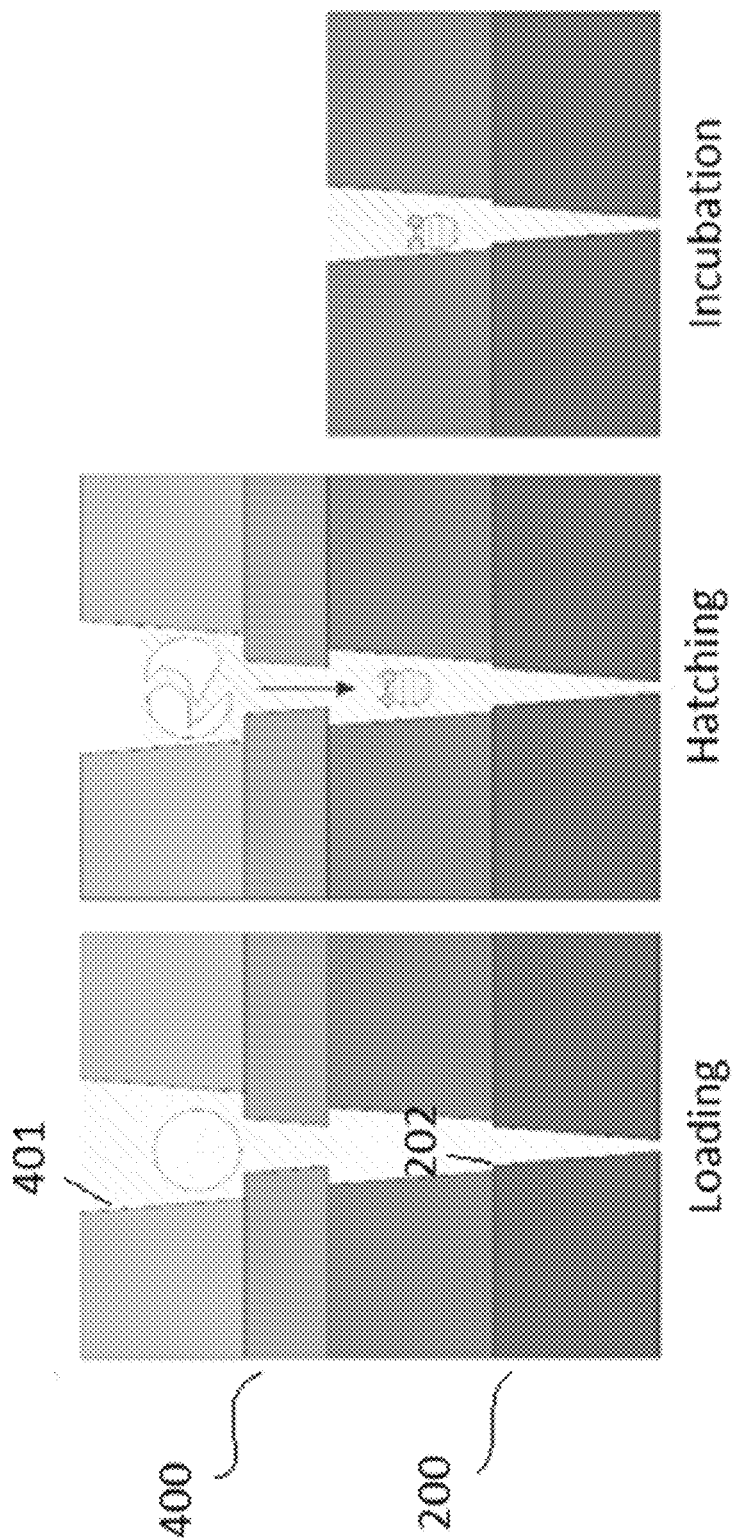
FIG. 12 illustrates the stacked loading layer and incubation layer according to certain embodiments of the present disclosure.
Figure 13:
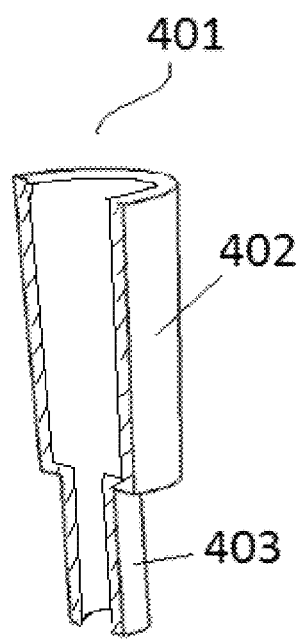
FIG. 13 illustrates a cut away view of a loading well according to certain embodiments of the present disclosure.

In certain embodiments, the microfluidic device 100 further comprises a loading layer 400 as shown in FIG. 11 for loading zebrafish larvae into the docks 201 of the incubation layer 200. The loading layer 400 is removably attached to the incubation layer 200 so that after the zebrafish larvae are loaded into the docks 201, the loading layer 400 can be removed. A loading layer 400 is helpful where zebrafish embryos instead of zebrafish larvae are used. Stacked loading layer 400 and incubation layer 200 are shown in FIG. 12. The loading layer 400 allows loading of zebrafish embryos and hatching of the embryos in the loading layer 400 and loading of hatched zebrafish larvae, but not the eggshells, from the loading layer 400 into the incubation layer 200 for incubation. As a result, fungicide and/or other chemicals required to prevent mold contamination caused by the eggshells can be dispensed with. The eggshells can be removed by simply removing the loading layer 400 plus an optional washing step. The loading layer 400 includes a plurality of wells 401 each in fluid communication with a respective tank 202 through the upper opening of the tank 202, so that a zebrafish larva can pass from a well 401 into the tank 202 of a corresponding dock 201. The well 401 has a stepped longitudinal cross-sectional shape in the y-z plane as shown in FIG. 13 dividing the well 401 into an upper well 402 and a lower well 403. The upper well 402 and the lower well 403 are of different geometries. The upper well 402 is generally larger than the lower well 403. The geometry of the upper well 402 is configured to accommodate a single embryo of a zebrafish, and to hatch the single embryo. For this purpose, the upper well 402 is sized large enough to accommodate one embryo but not so large to accommodate two or more embryos or to allow easy wash away of the embryo. The depth of the upper well 402 is large enough to prevent the embryo from being washed away but is not so large to allow stacking of two embryos in the upper well 402. The upper well 402 should avoid any cross-sectional shapes with sharp corner to avoid damage to the embryo. In certain embodiments, the upper well 402 has a circular horizontal cross-sectional shape with a diameter between 1.2 to 1.9 mm, 1.3 to 1.8 mm, 1.4 to 1.7 mm, or 1.5 to 1.6 mm. In certain embodiment, the diameter of an upper well 402 is 1.7±0.1 mm. However, other reasonable horizontal cross-sectional shapes and dimensions are also possible and within the contemplation of the present disclosure. Experiments show for an upper well 402 with a diameter of 1.73±0.016 mm, 97.9% of wells are occupied by a single embryo. By contrast, when the diameter of an upper well 402 is 1.46±0.015 mm, 24.3% of the wells are unoccupied as the diameter is too close to the average size of zebrafish embryos; when the diameter of an upper well 402 is 1.96±0.02 mm, multiple embryos can be loaded into the well and the successfully loaded embryos are easily washed away, resulting in unoccupied wells. It should be noted for other types of fish larvae or organisms, the same principles described above apply but different dimensions can be selected.

The geometry of the lower well 403 is configured for only the hatched larva of the embryo, but not the eggshells, to pass through the lower well 403 from the upper well 402 into a corresponding dock 201. For this purpose, the lower well 403 is sized slightly larger than the minimum dimension of the hatched zebrafish larva, but smaller than the average diameter of the embryo. In certain embodiments, the lower well 403 has a hollow cylindrical shape with a diameter in the range from 0.4-0.6 mm, such as 0.45 mm, 0.5 mm, or 0.55 mm. The lower well 403 should avoid any cross-sectional shapes with sharp corner to avoid damage to the larvae. It should be noted for other types of fish larvae or organisms, the same principles apply but different dimensions can be selected.

Fabrication of the Microfluidic Device

In certain embodiments, the microfluidic device 100 is fabricated using poly(methyl methacrylate) (PMMA) rather than PDMS which can have drug sorption issues.

In certain embodiments, the microfluidic device 100 can be designed by a computer aided design software (such as AutoCAD, Autodesk, USA). A commercial 50 W water-cooling laser system (K3323, Julong Laser Systems, China) can be used to cut polymethylmethacrylate (PMMA) sheets (Shengdalong Organic Glass Co., Ltd; China) with 65% power, 12 mm/s scanning speed and a computerized numerical control (CNC) milling machine (JINGYAN instrument, China) can be used to engrave microchannels (228±10 μm width and 179±13 μm depth) on PMMA surfaces with 10 degree V-tip carving tools. PMMA layers are cleansed by a soft brush, thoroughly rinsed and soaked in ddH$_2$O for 48 hours. After drying, the PMMA layers are carefully aligned and fastened in a C-clamp and the assembly is placed in a pre-heated oven for 20 mins at 110° C. for thermal bonding, thereby forming the microfluidic device. Six outlet syringes are connected to the microfluidic device through three-way valves that are used for water-level manipulation and three inlet syringes are directly connected to the microfluidic device. Inlet and outlet syringes are connected to the microfluidic device by Teflon tubing of 1.2 meters long and all the syringes and tubing are covered by aluminum foil throughout use.

Using the Microfluidic Device in Drug Screening Assay

Figure 14:
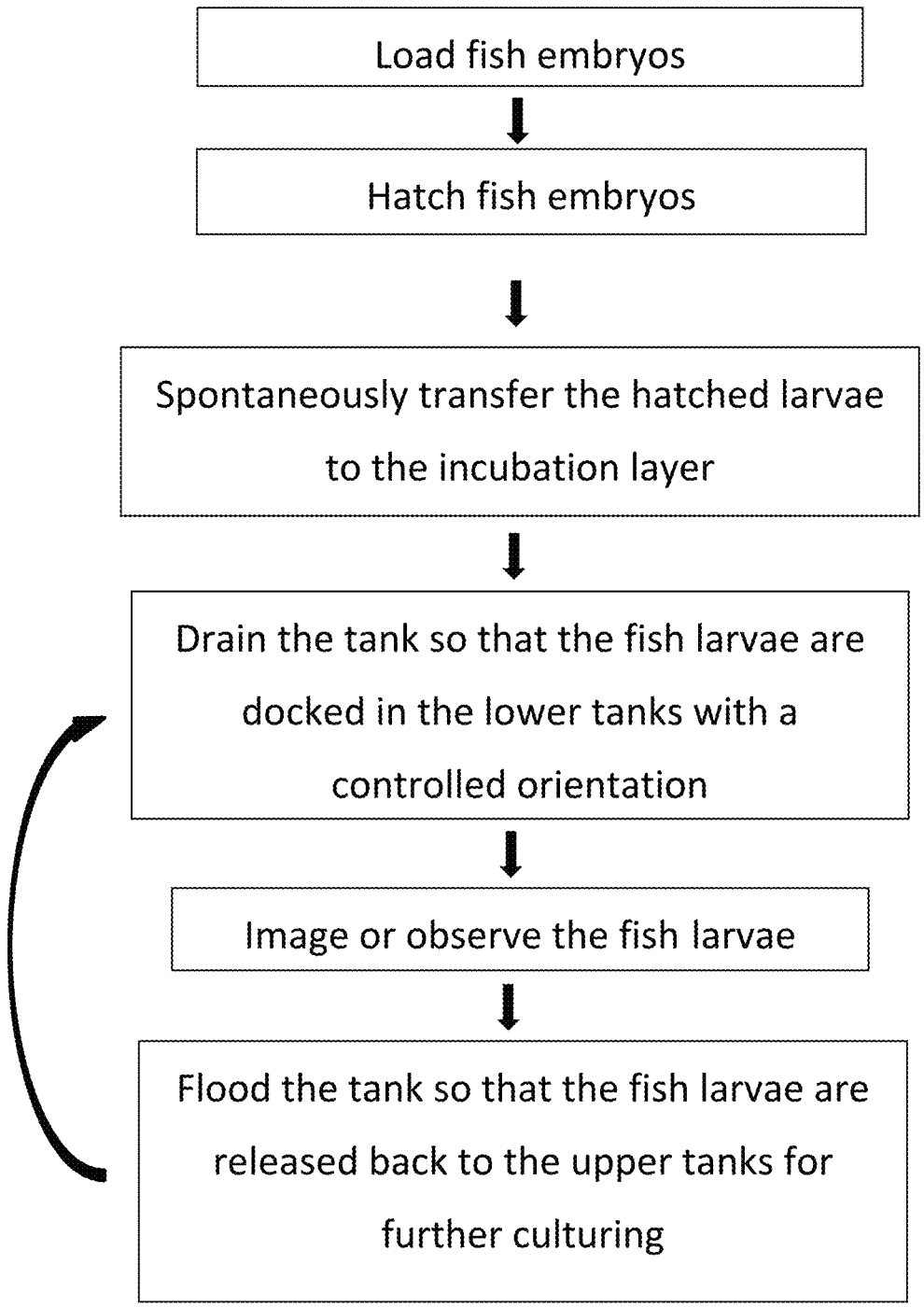
FIG. 14 illustrates a drug screening assay according to certain embodiments of the present disclosure.

A complete drug screening assay will now be described with reference to the microfluidic device of the present disclosure, as shown in FIG. 14. However, it should be noted that not all steps in the assay are necessary. For instance, where zebrafish larvae instead of embryos are used, the loading step can be dispensed with.

Loading and Hatching

In certain embodiments, the loading layer 400 is reversibly attached onto a microfluidic device 100 of the present disclosure to implement high-throughput embryo loading. The microfluidic device 100 can comprise an incubation layer 200 and a manifold layer 300, and is in fluid communication with an inlet pump 601 and an outlet pump 602. In certain embodiments, the loading layer 400 and a prefilled microfluidic device 100 are loosely held together by plastic screws, and the assembly is afloat on a dish of medium. Other arrangements are also possible and within the contemplation of the present disclosure. Loading can be achieved by simply pipetting drops of zebrafish embryos in a medium (e.g., about eighty embryos at an age of 48 hpf) on the surface of the loading layer. This loading process works analogous to gravity drainage where the vertical medium flow through the loading layer 400 aids the delivery of embryos into the stepped wells 401, such that a single embryo occupies each well 401 while excess medium is drained off through the gap between the loading layer 400 and the incubation layer 200. Once an upper well 402 is occupied by an embryo, excessive embryos can be easily washed away with fresh medium. Advantageously, the entire embryo loading process requires neither specialized skills nor a complicated or laborious procedure and is complete in about 30 seconds without applying suction or positive pressure. Moreover, this embryo loading method is highly scalable, because the time required to pipette over a loading layer 400 with wells 401 of higher density should be more or less the same.

After the loading process, the plastic screws can be fastened to allow incubation of the embryos on-chip for a hatching period of about 4 hours. Other hatching periods are possible, depending on the age of embryos loaded. Larvae transfer is spontaneous once the embryos are hatched. This on-chip hatching and spontaneous transfer can also act as a means to select larvae with decent motility, which is indicative of synchronized embryonic stage and fish viability. In certain embodiments, about 90% of zebrafish larvae are successfully transferred to the incubation layer 200 on average. After larvae transfer, the loading layer 400 can be detached from the incubation layer 200. In this way, all eggshells are removed in a single step and mold contamination is effectively prevented without using a fungicide.

Incubation and Observation

The fish larvae can be cultured and imaged in the docks 201. Upon removal of the loading layer 400, a cover layer 500 can be optionally stacked onto the microfluidic device 100. During this culturing and imaging process, the fish larvae are either temporarily "floating" in the upper tanks 203 or "docked" in the lower tanks 204 at a controlled orientation, as shown in FIGS. 5A and 5B. This is achieved by controlling the water level in the docks 201 by flooding or draining a medium. In this water-level control procedure, a zebrafish larva is analogous to a ship sitting in dry-dock when medium is drained, except that the zebrafish larva is still covered with medium in the lower tank 204. Since larvae are sensitive to and tend to move under lighting conditions (both bright field and fluorescence), it is very difficult, if not impossible, to render them immobile for, e.g., a 15-second video capture without proper orientation control using conventional techniques. With the microfluidic device of the present disclosure, however, it is possible to achieve orientation control/immobilize the zebrafish for, e.g., 15 second or above without the need of chemicals or anesthetics. After image capture, the medium is flooded into the stepped tanks 202 to raise the water level again so that zebrafish larvae refloat from the lower tanks 204 to the upper tanks 203 for further incubation without suffering from physical restrains inside the lower tanks 204. The docking and release states are easily interchangeable.

Another benefit of this water-level docking approach is its high scalability, as a large amount of larvae can be synchronously docked and refloated by a single event of flow control. In comparison with other microfluidic approaches, it is also easier to retrieve an individual larva for post-examination, because of the open access design of stepped tanks 202, where a cover layer 500 is not attached or has already been removed.

In certain embodiments, with a single step of solution draining, >70% of zebrafish larvae among all the tanks 202 are docked at the desired orientation. Multiple attempts can be made. Since this docking procedure is gentle and reversible, the desired orientation is attainable for >95% of zebrafish larvae among all the tanks 202 within three attempts.

In certain embodiments, all the functional series of docks 207 are flooded or drained simultaneously, so that the water-level control is conducted for all the functional series of docks 207 for imaging or observation.

In certain embodiments, such water-level control is separately conducted among the multiple functional series of docks 207. This is because taking 15-second videos for all stepped tanks 202 requires quite a long time (e.g., at least 15 minutes for a 48-tank microfluidic device, excluding the time for microscopic stage adjustment). In order to reduce the docking period and its disturbance to larvae, individual manipulation for a series of multiple stepped tanks 202 is possible.

In certain embodiments, High Performance Liquid Chromatography (HPLC) or Gas Chromatography-Mass Spectrometer (GC-MS) analysis and comparison between the compositional variation between fluid at the inlets 303 or entrances 502 and fluid at the exists 501 can be performed, so that the metabolism and absorption by the zebrafish larvae under different concentration of drugs, could provide extra pharmacological information in drug metabolism.

Structural Configuration of a Large-Scale Screening System

Figure 15:
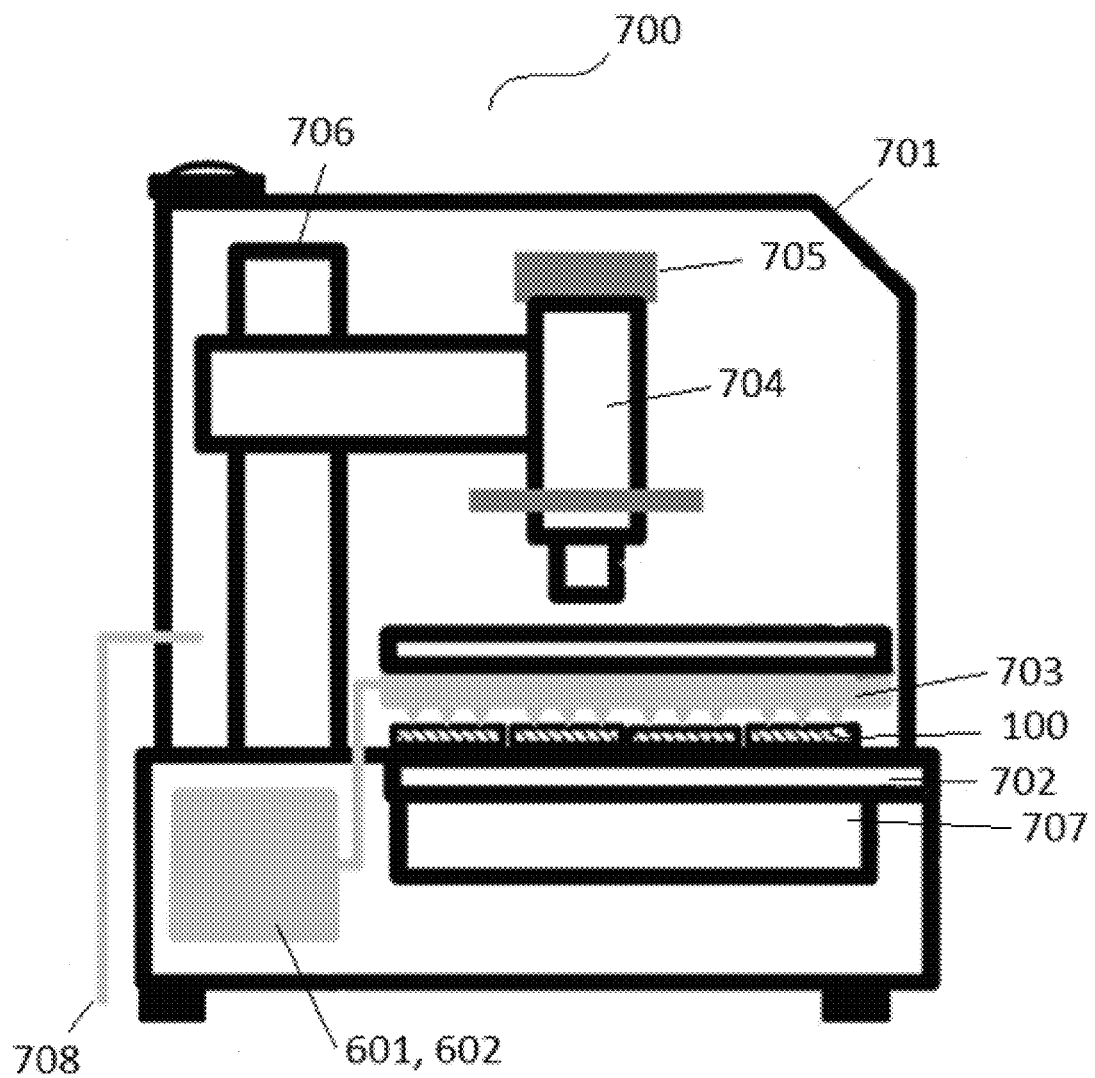
FIG. 15 illustrates a large-scale screening system according to certain embodiments of the present disclosure.

Another aspect of the present disclosure is a large-scale zebrafish screening system 700 as shown in FIG. 15. In certain embodiments, the screening system 700 incorporates a plurality of microfluidic devices 100 described above. These microfluidic devices 100 are accommodated in an enclosure 701 of the screening system. In certain embodiment, the enclosure 701 has a dimension of 30 cm (W)×40 cm (L)×40 cm (H), but other suitable dimensions are also possible and within the contemplation of the present disclosure. A chip cartridge 702 is provided in the enclosure 701 to secure the microfluidic devices 100 in a plane and align them with tubings on a tubing cassette 703 for fluid connections with inlet and outlet pumps 601, 602. In certain embodiments, the chip cartridge 701 can have a horizontal cross-sectional area of 200 mm×300 mm so it is capable of accommodating at least 40 individual microfluidic devices 100 of 25×60 mm in dimension. The tubing cassette 703 and the associated tubings allow quick fitting between the microfluidic devices 100 and the inlet and outlet pumps 601, 602.

In certain embodiments, the screening system 700 further comprises a microscope 704 (e.g. a monocular microscope) and a camera 705 (e.g. a CCD camera) mounted on a computer controlled XYZ axis frame 706, such that the microscope 704 and the camera 705 can move along any of the X, Y and Z axes to scan each tank 202 of the plurality of microfluidic devices 100 secured on the cartridge 702. This allows very high-throughput data acquisition. In certain embodiments, an excitation source and a bandpass filter (not shown) are arranged below the microfluidic devices 100 on the chip cartridge 702 such that fluorescence micrographs can be taken.

In certain embodiments, a temperature controller 707 is provided below the chip cartridge 702 so that the microfluidic devices 100 can be maintained at a temperature suitable for the hatching of zebrafish embryos or the culturing of zebrafish larvae. A gas inlet and outlet 708 can also be provided to ensure the atmosphere in the enclosure 701 is suitable for hatching or culturing.

The screening system 700 of the present disclosure is capable of simultaneously handling many more chips and many more individual fish docks 201 compared with existing designs having a similar footprint. In certain embodiments, with a full load of microfluidic devices 100, the screening system 700 is capable of handling up to 1,920 individual zebrafish larvae exposed to 240 different sets of drug gradients. More than 40 drugs or drug combinations could be examined at the same time. Almost all steps and experimental parameters (e.g., concentration, injection time, flow rate, temperature, etc.) can be automatically controlled and performed by a computer. The large-scale zebrafish screening system not only saves time for taking snapshots of individual fish docks, but also facilitates time course observation of zebrafish culture that normally requires continuous monitoring for 2 days, which is a great challenge in data collection by using conventional approaches.

Using of the Large-Scale Screening System in Drug Screening Assay

Below are examples of using the large-scale screening system of the present disclosure in high-throughput drug screen assay. In certain embodiments, the large-scale screening system can be used for monitoring responses of whole organisms or three-dimensional multicellular cell culture/spheroids under the stimulation of drugs, or to efficiently and accurately determine drug efficacy by time course normalization of the same fish. It should be understood, however, the description is only for illustrative not limiting purpose. The large-scale screening system of the present disclosure can be used for many other purposes.

Doxorubicin (Dox) is a known chemotherapeutic agent, but its clinical usage is limited due to its strong side effects. In the present disclosure, Dox serves as a model drug to stimulate zebrafish larva by its cardiotoxicity, i.e., to decrease the heart rate and trigger hemorrhage. 100 mg/L Dox and fish culture 0.2 mM Phenylthiourea (PTU) E3 medium are preloaded in an inlet pump and connected to a two-inlet gradient generator. The inlet pump is capable of keeping a stable flow to the gradient generator during the zebrafish culturing period. The gradient generator could create 6 different gradient concentrations by controlled laminar flow and diffusive mixing.

The embryos are obtained by random mating of wildtype fish. Fertilized eggs are collected and transferred to a Petri dish with E3 medium and maintained in an incubator at 28.5° C. After 24 hours, 0.2 mM Phenylthiourea (PUT) is added to E3 medium to inhibit melanisation of zebrafish. Zebrafish will normally break its eggshell in around 40 hpf (hours post fertilization) and 48 hpf larvae are transferred to the on-chip docks. There are 8 individual docks for each gradient, which could provide enough replication to examine dose effect of drug candidates. All docks will be enclosed by a breathable membrane secured by screws within the PMMA based chip and then transfers on mounting drawer of the device platform.

The tubing cassette is then inserted into the device platform to initialize tubing connections. After connection checking is completed, inlet and outlet pumps are started such that equal total flow rate is achieved (75 ml/h for inlets and 25 ml/h for outlet). The precise axis frame brings the camera and microscope in focus with the first fish dock for a clear view of the fish's beating heart.

Once the first fish dock location is determined, subsequent docks, either of the same functional series or a different functional series, will be automatically aligned by the software algorithm based on the chip design layout provided by the user. For cardiotoxicity, a short video clip of 20 seconds is taken for each larva for heart beat counting. The entire process is estimated to be completed within 10 mins for all 48 cultured fishes on a single chip, a remarkable contrast when comparing with a 10 mins data acquisition time for only 2-3 larvae by conventional methods. The on-chip examination of Dox cardiotoxicity requires drug treatment for 48 hours, just as the conventional methods do, but data can be collected in shortened intervals in the large-scale screening system of the present disclosure. Despite the level of this high throughput, it is also noteworthy that each time series is collected for the same larva in this platform, which is difficult, if not impossible, to achieve by conventional method.

Reagents

All chemicals and reagents are purchased from Sigma-Aldrich unless otherwise specified. Stock concentrations of 100 mM Doxorubicin (Dox) and 50 mM Diphenylurea (DPU) are prepared in dimethyl sulfoxide (DMSO). Three working solutions: 50 μM Dox only; 50 μM Dox & 5 μM DPU; 50 μM Dox & 0.1 μM DPU are freshly prepared before each experiment. 10 mM stock solution of Resorufin and Rhodamine 110 (R110) are prepared in DMSO and two working solutions are freshly prepared: 10 μM Resorufin & R110; 0.02 M Resorufin & R110. The E3 medium is prepared using the following recipe: 5 mM NaCl, 0.17 mM KCl, 0.33 mM CaCl2, 0.33 mM MgSO4 at pH 7.2-7.3. [20] 50× (10 mM) 1-phenyl-2-thiourea (PTU) stock is prepared in ddH2O and diluted with E3 medium to 1× working solution before use.

Zebrafish Maintenance

Tg(cmlc2: GFP) transgenic zebrafishes were maintained in accordance to the Zebrafish Handbook. Adult fish were raised at 28° C. in an aquaculture system under a 12/12 hours (Light/Dark) cycle and fed with newly hatched brine shrimp at 10:00 and 17:00 twice daily. Male and female fish were cultured separately. Healthy 1 year old adult fish were randomly picked at a ratio of 2 females to 3 males and placed in a small tank separated by a divider overnight. The divider was removed when the light was turned on in the morning for fish mating. The fertilized eggs were collected with the help of a tea strainer and transferred to Petri dishes filled with E3 medium at 28° C. The embryos were primarily screened at 8 hpf (hours post fertilization) and 24 hpf based on their stages in embryogenesis under a stereomicroscope (Olympus SZX12). Pigmentation was inhibited by adding 0.2 mM PTU in the E3 medium to facilitate fluorescence observation of the embryos and larvae. All animal experiments were conducted according to the ethical guideline approved by Institute of Chinese Medical Science in the University of Macau.

Embryos Loading, On-Chip Hatching and Spontaneous Transfer

The loading layer was attached with the incubation layer by a pair of plastic screws and the inlets and outlets are connected to two multichannel syringe pumps (SPLab10 & SPLab12, Baoding Shenchen precision pump Co., LTD). A flow rate of 1000 μL·h-1 was used to prime the microfluidic device for 30 mins with E3 medium. For embryo loading, syringe pumps were paused and the microfluidic device is allowed to float on the dish of E3 medium and drops of embryos (randomly picked~80 embryos at 48 hpf) were manually pipetted on top of the loading layer followed by washing with E3 medium to remove excessive embryos. After loading, the plastic screws were tightened and on-chip incubation and hatching occurs in period of 4 hours after which the loading layer is detached. The assembly was kept in a humidity box inside a high precision temperature incubator (MIR-254-PE, Panasonic, Japan) at 28° C. Infusion and withdrawal rates were reduced to 46 μL·h-1 and 22 μL·h-1 during the incubation period.

Video Capture and Snapshot Imaging with On-Chip Dorsal Orientation Control

The flooding and draining process was controlled by six outlet syringes with each connecting a 3-way valve. In video capture mode, each functional series of docks was allowed to drain separately. FIG. 10 depicts a first valve that is set to drain a single series of stepped tanks connecting to outlet syringe. The other 3-way valves were switched so that outlet syringes were connected with the medium reservoir instead of draining solution from the incubation layer. A fixed dispensing volume of 85 μL at a backward flow rate of 5.6 μL s$^{-1}$ was used to lower the water level among the upper tanks to the docking state. By manual inspection under a fluorescence microscope using a 20× objective lens (Olympus IX73 inverted microscope equipped with a DP72 digital camera, Japan), a 15-second video clip was taken for each larva having proper orientation. A maximal of three water-level control attempts were used to correct larvae orientation. After video capture for the functional series of docks, the same dispensing volume and a forward flow rate of 5.6 µL s$^{-1}$ was used to refill the stepped tanks. Likewise, the manipulation of a second functional series of stepped tanks was achieved by switching the 3-way valves. In a snapshot mode, all functional series of stepped tanks were synchronously manipulated to improve the efficiency in image acquisition.

DPU Protect Dox Induced Zebrafish Cardiotoxicity

Transgenic Tg (cmlc2:GFP) zebrafishes were used for cardiotoxicity assays. All embryos were incubated in E3 medium containing 0.2 mM PTU from 24 hpf. Zebrafish embryos of 48 hpf were allowed to load, incubate and spontaneously hatched as described in previous section. During the incubation period from 48-96 hpf, infusion (46 µL·h$^{-1}$) and withdrawal (22 µL·h-1) rates were used to load E3 medium with 0.2 mM PTU into the device. For drug administration from 96 hpf to 144 hpf, inlet syringe contents were swapped to drug solution (50 µM Dox only; 50 µM Dox & 0.1 µM DPU; 50 µM Dox & 5 µM DPU). Quantitative assessment of cardiac function was obtained by recording a 15-sec video clip for each fish at 12-hour intervals. Frames extracted from the video clips were used to measure the lateral axis length between the myocardial borders of ventricles at end-diastolic and end-systolic states. The percentage fractional shortening (% FS) was calculated with the following formula: (diastolic lateral axis length–systolic lateral axis length)/(diastolic lateral axis length)× 100%.

Statistical Analysis

One-way Analysis of Variance (ANOVA) with Tukey's multiple comparison test was performed by Origin Pro 2017 (OriginLab Corporation, U.S.A.) to test for significant difference. The use of star * indicated the significance level of $P \leq 0.01$.

Figure 16:
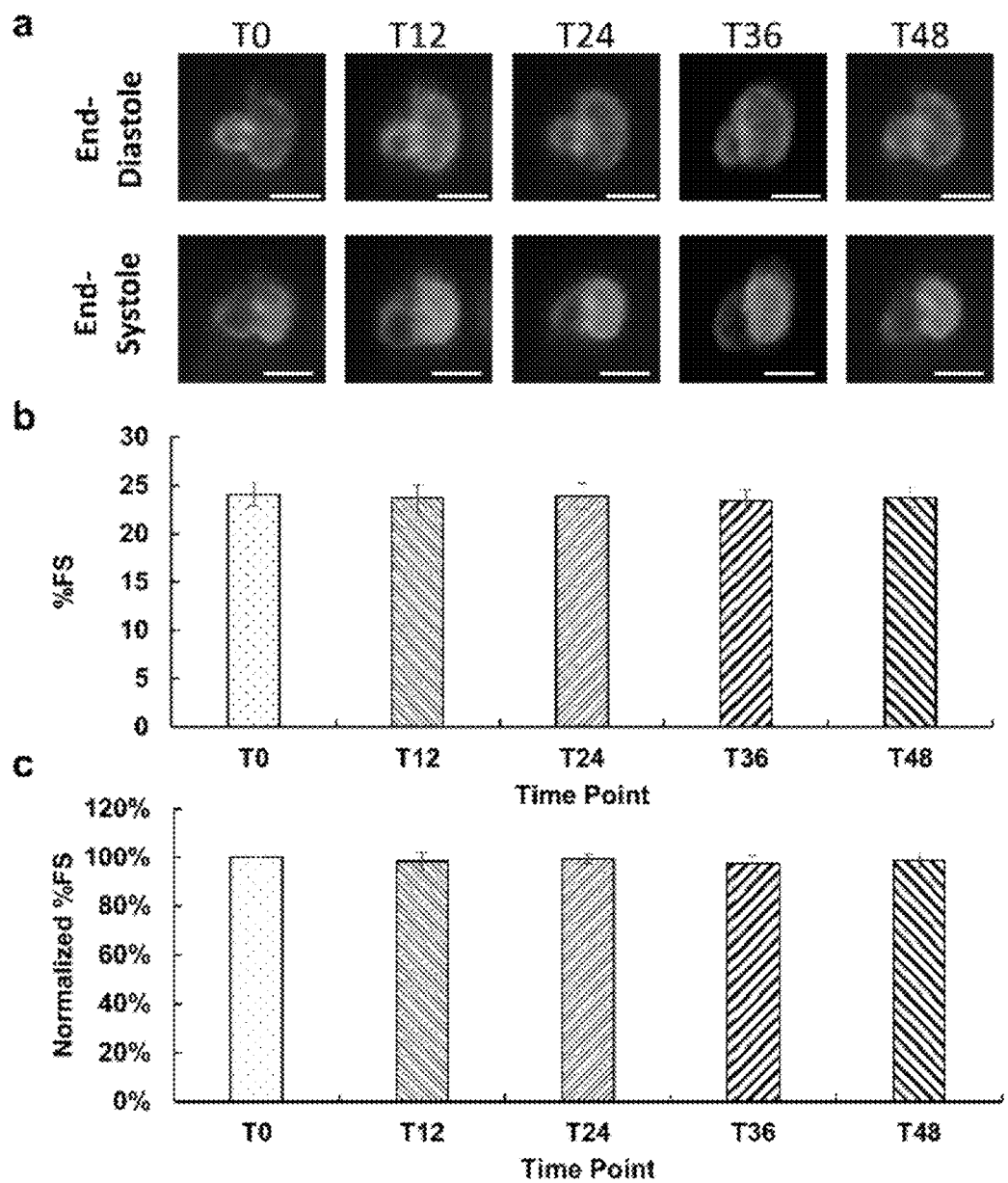
FIG. 16 shows the tracking of cardiac function of the same zebrafish heart through 48-hour time-course experiment.

FIG. 16(a) shows a series of end-diastolic and end-systolic fluorescent micrographs of the same zebrafish heart that were taken at 12-hour intervals along a time course of 48 hours in E3 medium. These images were frames extracted from 15-second video clips of the corresponding time points. Typically, four metrics are representative of cardiac function: heart rate (HR), the stroke volume (SV), cardiac output (CO) and the percent fractional shortening (% FS). While HR, SV and CO have relatively high dependency on the absolute cardiac sizes, % FS measures the myocardial contractility in a ratiometric manner that has taken into account the heterogeneity of cardiac sizes among zebrafishes in a population. Thus, % FS is chosen to be the metric for the following analysis. Results in FIG. 16(b) shows the mean % FS values among 15 larvae and their cardiac function was stable throughout the course of experiment. Since the time points in each set of the time course experiment were obtained from the same heart of an individual larva within this device, the data can be further processed by normalizing each set of time course results by the T0 data of the same fish, as shown in FIG. 16(c).

Figure 17:
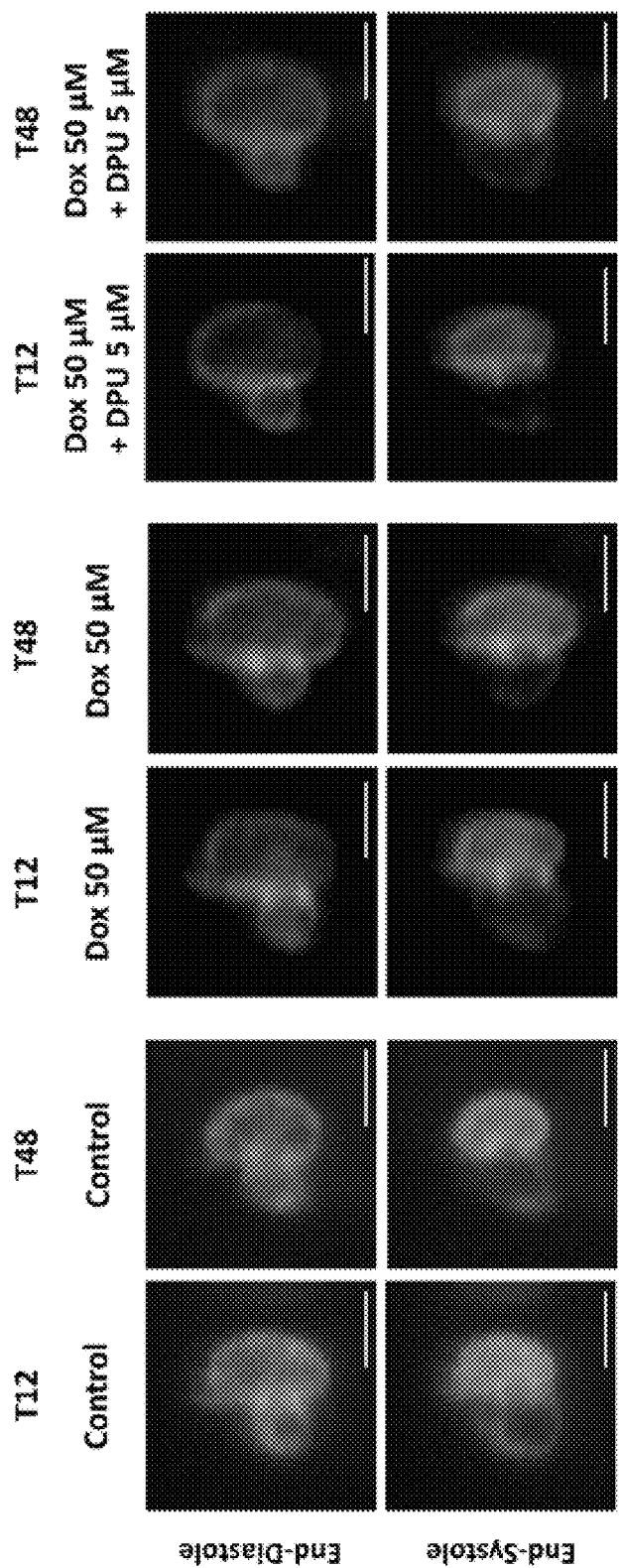
FIG. 17 is fluorescent images showing the dose-dependent protective effect of DPU on doxorubicin-induced cardiomyopathy.
Figure 18:
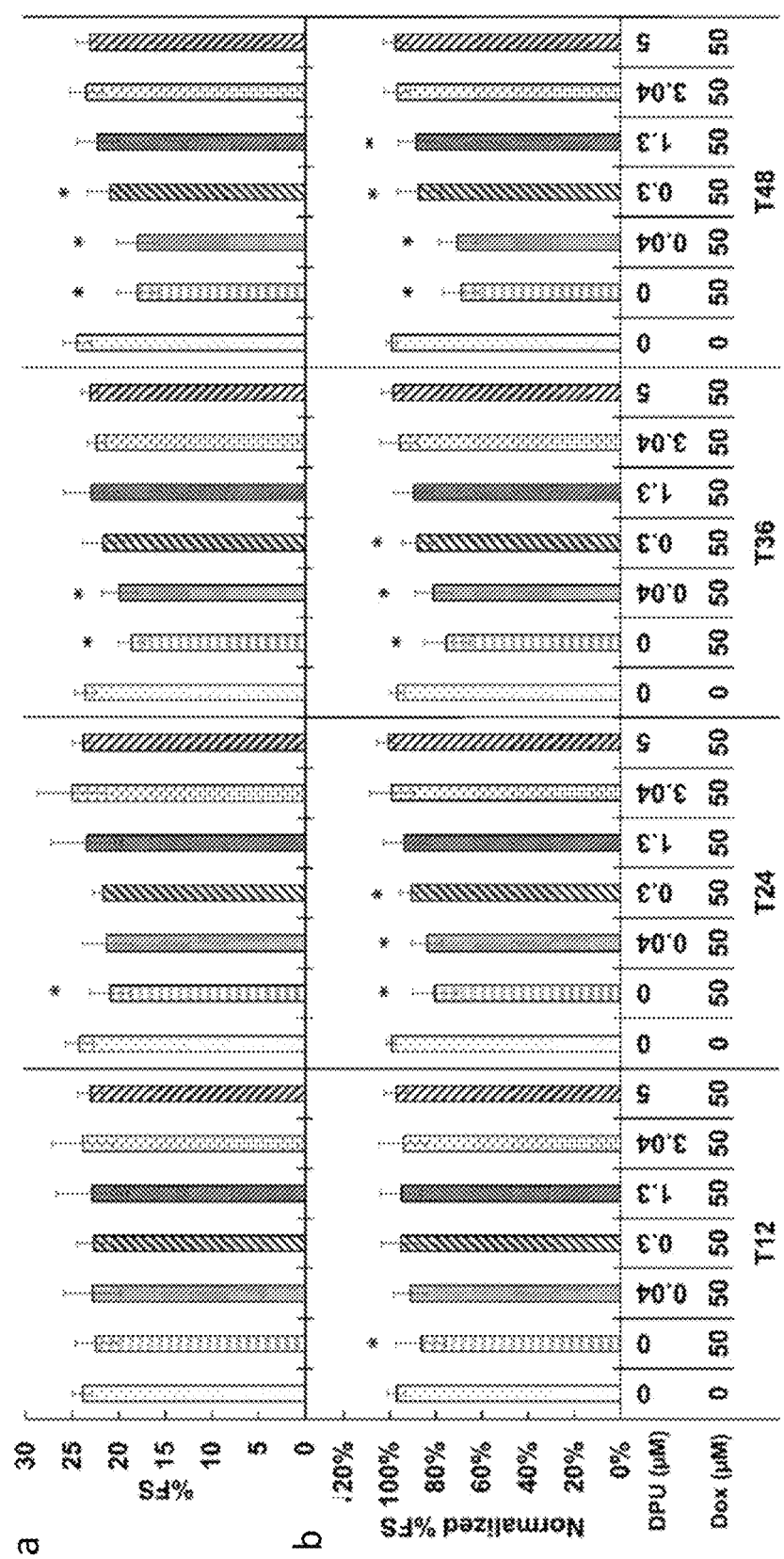
FIG. 18 shows the dose-dependent protective effect of DPU on doxorubicin-induced cardiomyopathy.

Using an on-chip gradient generator with three inlets, different initial drug concentrations were diluted and dispensed into six functional series of docks (a fixed 50 µM of Dox co-treated with gradient concentrations of DPU: 5; 3.04; 1.3; 0.3; 0.04; 0 µM). Dose-dependent protective effects of DPU on Dox-induced cardiomyopathy are illustrated in FIG. 18(a). Representative images of the same zebrafish heart at T12 and T48 are compared among each other under different drug treatment, as shown in FIG. 17, in which the myocardial contractility of the group co-treated with Dox+DPU is similar to the control group at T48. Quantitative results of % FS in Dox treated larvae under different doses of DPU and time course normalization of the same results are illustrated in FIGS. 18(a) and 18(b), respectively. In conventional studies, dose response are usually illustrated at a single time point, as in T48 of FIG. 16(b), where there is no statistical difference among the control and treatment groups incubated with 1.3 µM or higher DPU concentrations. In other words, at least 1.3 M DPU was required to protect against doxorubicin-induced cardiomyopathy, which is comparable with literature results. Remarkably, the dose dependency obtained from 48-hour drug treatment (T48 of FIG. 18(a)) can be revealed in 24 hours by normalizing the results of the same zebrafishes (T24 of FIG. 18(b)). Furthermore, by comparing each and every time point between FIGS. 18(a) and 18(b), more treatment groups are found to have statistical difference between their corresponding control groups.

By normalizing the results retrieved from the same larva at multiple time points, the individual heterogeneity towards drug sensitivity can be correlated to unravel the intrinsic dose dependency earlier than using the same results without normalization. As this time course normalization approach requires a shorter period of drug treatment to reach similar conclusion in dose dependency and reveals the statistical difference of more treatment groups using in each time point, it is a more efficient and accurate way to decipher the intrinsic dose responses for drug screening. Since each larva is sacrificed at each time point, 4 times the amount of larvae are needed to be sacrificed by conventional approach in order to interrogate all the time points that have been traced through the microfluidic approach.

Although the invention has been described in terms of certain embodiments, other embodiments apparent to those of ordinary skill in the art are also within the scope of this invention. Accordingly, the scope of the invention is intended to be defined only by the claims which follow.

The invention claimed is:

1. A microfluidic device, comprising:
   an incubation layer, the incubation layer including:
      at least one dock, each of the at least one dock defines a stepped tank comprising an upper tank and a lower tank, an inflow channel in fluid communication with the stepped tank for supplying a fluid to the stepped tank, and an outflow channel in fluid communication with the stepped tank for draining the fluid from the stepped tank,
   wherein the geometry of the upper tank is configured to allow culturing of a fish larva therein, and
   wherein the geometry of the lower tank is configured to reversibly receive the fish larva from the upper tank and to dock the fish larva at a controlled orientation for imaging or observation.

2. The microfluidic device according to claim 1, wherein the geometry of the lower tank fits the dimension of the fish larva so that the fish larva assumes a dorsal or ventral orientation when it is received in the lower tank.

3. The microfluidic device according to claim 1, wherein the outflow channel is arranged above the inflow channel, optionally the inflow channel is in fluid communication with the lower tank, and the outflow channel is in fluid communication with the upper tank.

4. The microfluidic device according to claim 1, wherein the lower tank has an inverted trapezoidal or a V shaped longitudinal cross-section.

5. The microfluidic device according to claim 1, wherein the lower tank has a width of 0.3-0.5 mm, and the upper tank has a width of 0.8-0.9 mm.

6. The microfluidic device according to claim 1, wherein the outflow channel is further configured to supply the fluid to the stepped tank.

7. The microfluidic device according to claim 1, wherein the incubation layer comprises a plurality of functional series of docks, each of the plurality of functional series of docks comprises a plurality of docks, an inlet port in fluid communication with the inflow channels of the plurality of docks, and an outlet port in fluid communication with the outflow channels of the plurality of docks.

8. The microfluidic device according to claim 7, further comprising:
a manifold layer, the manifold layer including:
at least two inlets in fluid communication with at least two external fluid sources for receiving at least a first component and a second component of the fluid;
a plurality of outlets, each of the plurality of outlets is in fluid communication with the inlet port of a respective functional series of docks; and
a manifold structure in fluid communication with the at least two inlets and the plurality of outlets.

9. The microfluidic device according to claim 8, wherein the manifold structure comprises a gradient generator, the gradient generator is configured to receive the first component and the second component of the fluid from the at least two inlets and deliver to the plurality of outlets mixtures of the first component to the second component at various ratios.

10. The microfluidic device according to claim 9, wherein the manifold layer further comprises a flooding structure, the flooding structure has a plurality of branches, each of the plurality of branches is in fluid communication with the gradient generator and a respective outlet of the plurality of outlets.

11. The microfluidic device according to claim 8, further comprising a cover layer with a plurality of exits, each of the plurality of exits is in fluid communication with the outlet port of a respective functional series of docks.

12. The microfluidic device according to claim 11, wherein a same fluidic resistance is achieved in each fluidic path between each of the at least two inlets of the manifold layer and a corresponding exit of the cover layer.

13. The microfluidic device according to claim 11, wherein the at least two inlets of the manifold layer are in fluid communication with at least one inlet pump, the plurality of exits of the cover layer are in fluid communication with at least one outlet pump, and the at least one inlet pump and the at least one outlet pump can be operated at the same or different flow rates.

14. A drug screening assay using the microfluidic device according to claim 13 with a fish larva in each dock, wherein the assay comprising the steps of:

a) draining the fluid from the stepped tanks to lower the water level below the upper tanks so that the fish larvae are docked in the lower tanks with a controlled orientation;
b) imaging or observing the fish larvae for an observing period;
c) flooding the fluid to the stepped tanks to leverage the water level above the lower tanks so that the fish larvae are released to the upper tanks for further culturing; and
d) optionally repeating steps a) to c).

15. The microfluidic device according to claim 11, wherein a 3-way valve can be in fluid communication with an exit of the cover layer, a respective outlet pump, and a medium reservoir.

16. The microfluidic device according to claim 8, further comprising:
a loading layer, the loading layer including:
a plurality of stepped wells each in fluid communication with a respective dock, each of the plurality of stepped wells comprising an upper well and a lower well,
wherein the geometry of the upper well is configured to accommodate a single embryo of a fish;
wherein the geometry of the lower well is configured so that only the hatched larva of the embryo is capable of passing through the lower well from the upper well into the respective dock.

17. The microfluidic device according to claim 16, wherein the upper well of each of the plurality of stepped wells has a hollow cylindrical shape with a diameter in the range from 1.46 mm to 1.96 mm.

18. The microfluidic device according to claim 16, wherein the lower well of each of the plurality of stepped wells has a hollow cylindrical shape with a diameter in the range from 0.4 mm to 0.6 mm.

19. A drug screening assay using the microfluidic device according to claim 16, wherein the assay comprising the steps of:
a) applying drops of fish embryos onto the loading layer;
b) incubating the fish embryos in the stepped wells of the loading layer for a hatching period;
c) hatching and spontaneously transferring the hatched larvae from the stepped wells of the loading layer to the stepped tanks of the incubation layer;
d) removing the loading layer from the remaining parts of the microfluidic device;
e) draining the fluid from the stepped tanks to lower the water level below the upper tanks so that the fish larvae are docked in the lower tanks with a controlled orientation;
f) imaging or observing the fish larvae for an observing period;
g) flooding the fluid to the stepped tanks to leverage the water level above the lower tanks so that the fish larvae are released back to the upper tanks for further culturing; and
h) optionally repeating steps e) to g).

20. The drug screening assay according to claim 19, comprising between steps a) and b) a further step i) of washing away unloaded embryos with a medium.

* * * * *